United States Patent [19]

Jaeggi et al.

[11] 4,139,623
[45] Feb. 13, 1979

[54] CYCLIC-SUBSTITUTED DERIVATIVES OF 1-AMINO-2-PROPANOL

[75] Inventors: Knut A. Jaeggi, Basel; Franz Ostermayer, Riehen; Herbert Schroter, Füllinsdorf, all of Switzerland

[73] Assignee: C-G Corp., Ardsley, N.Y.

[21] Appl. No.: 777,222

[22] Filed: Mar. 14, 1977

Related U.S. Application Data

[62] Division of Ser. No. 574,785, May 5, 1975, Pat. No. 4,027,027.

[30] Foreign Application Priority Data

May 14, 1974 [CH] Switzerland .................. 6582/74

[51] Int. Cl.$^2$ .................. A61K 31/505; C07D 239/34
[52] U.S. Cl. .................. 424/251; 424/266; 424/250; 424/263; 544/295; 544/296; 544/357; 544/408; 544/111; 544/359
[58] Field of Search .................. 260/256.4 C; 424/251; 544/316

[56] References Cited

U.S. PATENT DOCUMENTS

| | | | |
|---|---|---|---|
| 3,888,898 | 6/1975 | Koppe et al. | 260/256.4 C |
| 3,940,406 | 2/1976 | Raabe et al. | 260/295 AM |

*Primary Examiner*—Jose Tovar
*Assistant Examiner*—James H. Turnipseed
*Attorney, Agent, or Firm*—John J. Maitner

[57] ABSTRACT

Compounds of the formula

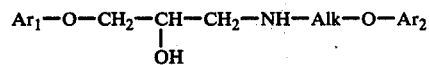

$$Ar_1-O-CH_2-CH-CH_2-NH-Alk-O-Ar_2$$
$$\underset{OH}{|}$$

wherein $Ar_1$ and $Ar_2$ denote an optionally substituted aromatic hydrocarbon radical or a monocyclic, monoazacyclic or diazacyclic radical of aromatic character and Alk represents lower alkylene, or salts thereof, exhibit $\beta$-receptor-blocking, blood pressure-lowering and vasodilatory effects and are useful for example in the treatment of arrythmias and angina pectoris, and as blood pressure-lowering agents.

7 Claims, No Drawings

CYCLIC-SUBSTITUTED DERIVATIVES OF 1-AMINO-2-PROPANOL

This is a division of application Ser. No. 574,785, filed May 5, 1975, now U.S. Pat. No. 4,027,027.

The present invention relates to cyclic-substituted derivatives of 1-amino-2-propanol, of the formula

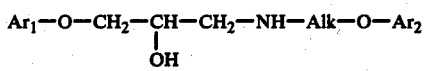

$$Ar_1-O-CH_2-\underset{OH}{CH}-CH_2-NH-Alk-O-Ar_2 \quad (I)$$

wherein $Ar_1$ and $Ar_2$ denote an optionally substituted aromatic hydrocarbon radical or a monocyclic monoazacyclic or diazacyclic radical, of aromatic character, which is optionally substituted and is bonded to the oxygen atom via a ring carbon atom, with the proviso that at least one of the radicals $Ar_1$ and $Ar_2$ represents a monocyclic, monoazacyclic or diazacyclic, radical of aromatic character which is optionally substituted and is bonded to the oxygen atom via a ring carbon atom and Alk represents lower alkylene which separates the nitrogen atom from the oxygen atom by at least two carbon atoms, or salts thereof and processes for their preparation, as well as pharmaceutical preparations containing such compounds, and their use.

The radical $Ar_1$ is above all a monocyclic aromatic hydrocarbon radical, that is to say phenyl, but can also represent a bicylic aromatic hydrocarbon radical, that is to say 1-naphthyl or 2-naphthyl. Such radicals are preferably monosubstituted, disubstituted or polysubstituted. Substituents of such radicals $Ar_1$ are, in particular, monovalent substituents, such as optionally substituted hydrocarbon radicals, of aliphatic character, for example optionally substituted aliphatic or cycloaliphatic hydrocarbon radicals, such as optionally substituted lower alkyl, lower alkenyl or lower alkinyl, possible substituents of such radicals, and especially of lower alkyl, being above all etherified hydroxyl or mercapto, such as lower alkoxy or lower alkylthio, or acylated amino, such as lower alkanoylamino or lower alkoxycarbonylamino, etherified hydroxyl or mercapto groups, above all hydroxyl or mercapto groups etherified by optionally substituted aliphatic hydrocarbon radicals, such as optionally substituted lower alkoxy, lower alkenyloxy, lower alkinyloxy or lower alkylthio, possible substituents being above all etherified hydroxyl or mercapto, such as lower alkoxy or lower alkylthio, or acylated amino, such as lower alkanoylamino or lower alkoxycarbonylamino, halogen, nitro, acylated amino, such as lower alkanoylamino, lower alkoxycarbonylamino or optionally N-substituted carbamoylamino, for example ureido, N'-lower alkyl-ureido or N,N'-di-lower alkyl-ureido, or optionally functionally modified carboxyl, such as esterified carboxyl, for example lower alkoxycarbonyl, amidised carboxyl, for example carbamoyl, N-lower alkyl-carbamoyl or N,N-di-lower alkylcarbamoyl, or cyano, as well as divalent substituents which substitute two different ring carbons of the radical $Ar_1$, such as an optionally substituted divalent aliphatic hydrocarbon radical which can optionally be interrupted by one or more chain heteroatoms, such as nitrogen atoms or oxygen atoms, for example lower alkylene or lower alkenylene, aza-lower alkylene, for example 1-aza-1,3-prop-2-enylene, or dioxa-lower alkylene, for example lower alkylidenedioxy or lower alkylenedioxy.

The radical $Ar_2$ is above all optionally substituted pyridyl, for example 2-, 3- or 4-pyridyl, as well as optionally substituted pyridazinyl, for example 3- or 4-pyridazinyl, pyrimidinyl, for example 2-, 4- or 5-pyrimidinyl, or pyrazinyl, for example 2-pyrazinyl. Such radicals are preferably monosubstituted, disubstituted or polysubstituted. Substituents of such heterocyclic radicals are above all monovalent substituents, such as optionally substituted aliphatic hydrocarbon radicals, for example optionally substituted lower alkyl, possible substituents being above all acylated amino, such as lower alkanoylamino or lower alkoxycarbonylamino, or optionally functionally modified carboxyl, such as esterified carboxyl, for example lower alkoxy carbonyl, or amidised carboxyl, such as optionally N-mono- or N,N-di-lower alkylated carbamoyl, or cyano, optionally etherified or esterified hydroxyl, for example lower alkoxy or halogen, nitro, acylated amino, such as lower alkanoylamino, lower alkoxycarbonylamino or optionally N-substituted carbamoylamino, for example ureido, N'-lower alkyl-ureido or N',N'-di-lower alkyl-ureido, or optionally functionally modified carboxyl, such as esterified carboxyl, for example lower alkoxycarbonyl, amidised carboxyl, for example carbamoyl, N-lower alkylcarbamoyl or N,N-di-lower alkylcarbamoyl, or cyano.

The radical $Ar_2$ is furthermore above all a monocyclic aromatic hydrocarbon radical, that is to say phenyl, but can also be optionally substituted pyridyl, for example 2-, 3- or 4-pyridyl, as well as optionally substituted pyridazinyl, for example 3- or 4-pyridazinyl, pyrimidinyl, for example 2-, 4- or 5-pyrimidinyl, or pyrazinyl, for example 2-pyrazinyl. The above radicals $Ar_2$ are preferably monosubstituted, disubstituted or polysubstituted. Substituents of such heterocyclic radicals are, above all, monovalent substituents, such as optionally substituted aliphatic hydrocarbon radicals, for example optionally substituted lower alkyl, possible substituents being above all acylated amino or lower alkanoylamino or lower alkoxycarbonylamino, or optionally functionally modified carboxyl, such as esterified carboxyl, for example lower alkoxycarbonyl, or amidised carboxyl, such as optionally N-mono- or N,N-di-lower alkylated carbamoyl, or cyano, optionally etherified or esterified hydroxyl, for example lower alkoxy or halogen, nitro, acylated amino, such as lower alkanoylamino, lower alkoxycarbonylamino or optionally N-substituted carbamoylamino, for example ureido, N'-lower alkylureido or N',N'-di-lower alkylureido, or optionally functionally modified carboxyl, such as esterified carboxyl, for example lower alkoxycarbonyl, amidised carboxyl, for example carbamoyl, N-lower alkylcarbamoyl or N,N-di-lower alkylcarbamoyl, or cyano.

The radical $Ar_2$ is furthermore above all optionally substituted pyridyl, for example 2-, 3- or 4-pyridyl, as well as optionally substituted pyridazinyl, for example 3- or 4-pyridazinyl, pyrimidinyl, for example 2-, 4- or 5-pyrimidinyl or pyrazinyl, for example 2-pyrazinyl. Such radicals are preferably monosubstituted, disubstituted, or polysubstituted. Substituents of such heterocyclic radicals are above all monovalent substituents, such as optionally substituted aliphatic hydrocarbon radicals, for example, optionally substituted lower alkyl, possible substituents being, for example, optionally substituted, especially acylated, amino, such as lower alkanoylamino or lower alkoxycarbonylamino, optionally etherified hydroxyl or mercapto, such as lower alkoxy or lower alkylthio, or optionally functionally modified carboxyl, such as esterified carboxyl, for example lower alkoxycarbonyl, or amidised carboxyl, such as optionally N-mono- or N,N-di-lower alkylated carbamoyl, or cyano, optionally functionally modified, for example etherified or esterified, hydroxyl or mercapto, such as lower alkoxy, lower alkenyloxy, lower alkoxy-lower alkoxy, lower alkylthio or halogen, nitro, optionally substituted amino, such as lower alkylamino or di-lower alkylamino, lower alkyleneamino, oxa-lower alkyleneamino, aza-lower alkyleneamino or acylated amino, such as lower alkanoylamino, lower alkoxycarbonylamino or optionally N-substituted carbamoylamino, for example ureido, N'-lower alkyl-ureido or N',N'-di-lower alkyl-ureido, or optionally functionally modified carboxyl, such as esterified carboxyl, for example lower alkoxycarbonyl, amidised carboxyl, for example carbamoyl, N-lower alkylcarbamoyl or N,N-di-lower alkylcarbamoyl, or cyano.

The lower alkylene group Alk can be straight or branched, preferably has up to 7, above all up to 4, carbon atoms, and separates the nitrogen atom from the oxygen atom by at least 2, preferably by 2–3 and above all by 2 carbon atoms.

The general expressions used within the scope of the present application have the meaning shown below unless defined otherwise, and groups and compounds designated as "lower" preferably contain up to 7 and above all up to 4 carbon atoms.

Lower alkyl is, for example, methyl, ethyl, n-propyl, isopropyl, n-butyl, isobutyl, sec.-butyl, tert.-butyl, n-pentyl, neopentyl, n-hexyl or n-heptyl, whilst lower alkenyl represents, for example, vinyl, allyl or methallyl, and lower alkinyl represents, for example, ethinyl or propargyl.

Lower alkoxy is, for example, methoxy, ethoxy, n-propoxy, isopropoxy, n-butoxy, isobutoxy or tert.-butoxy, lower alkenyloxy is, for example, allyloxy or methallyloxy, and lower alkinyloxy is, for example, propargyloxy.

Lower alkylthio represents, for example, methylthio, ethylthio, n-propylthio or isopropylthio.

Halogen is above all halogen of atomic number up to 35, that is to say fluorine, chlorine or bromine.

Lower alkanoyl is, for example, acetyl, propionyl or pivaloyl.

Lower alkanoylamino is, for example, acetylamino, propionylamino or pivaloylamino, and lower alkoxycarbonylamino is, for example, methoxycarbonylamino, ethoxycarbonylamino, n-propoxycarbonylamino, isopropoxycarbonylamino or n-butoxycarbonylamino, whilst N'-lower alkyl-ureido and N',N'-di-lower alkyl-ureido represent, for example, N'-methyl-ureido, N'-ethyl-ureido or N',N'-dimethyl-ureido.

Lower alkoxycarbonyl is, for example, methoxycarbonyl, ethoxycarbonyl, n-propoxycarbonyl or isopropoxycarbonyl.

N-Lower alkylcarbamoyl is, for example, N-methylcarbamoyl, N-ethylcarbamoyl, N-n-propylcarbamoyl, N-n-butylcarbamoyl or N-n-hexylcarbamoyl, and N,N-di-lower alkyl-carbamoyl is, for example, N,N-dimethylcarbamoyl or N,N-diethylcarbamoyl.

Lower alkyl substituted by hydroxyl and lower alkoxy is, for example, hydroxymethyl and 2-hydroxyethyl, and also, above all, oxa-lower alkyl, for example methoxymethyl, ethoxymethyl, 2-methoxyethyl or 2-ethoxyethyl, whilst lower alkyl substituted by lower alkylthio is thia-lower alkyl, for example methylthiomethyl, ethylthiomethyl, 2-methylthioethyl or 2-ethylthioethyl. Lower alkyl substituted by lower alkanoylamino is, for example, acetylaminomethyl, 2-acetyl-aminoethyl, 2-propionylaminoethyl or 2-pivaloylaminoethyl, and lower alkyl substituted by lower alkoxycarbonylamino is, for example, methoxycarbonylaminomethyl, ethoxycarbonylaminomethyl, 2-methoxycarbonylaminoethyl or 2-ethoxycarbonylaminoethyl. Lower alkenyl substituted by lower alkanoylamino is, for example, 2-acetylamino-vinyl or 2-propionylamino-vinyl and lower alkenyl substituted by lower alkoxycarbonylamino is, for example, 2-methoxycarbonylamino-vinyl or 2-ethoxycarbonylamino-vinyl.

Lower alkoxy substituted by lower alkoxy is above all oxa-lower alkoxy, for example 2-methoxy-ethoxy or 2-ethoxy-ethoxy, whilst lower alkoxy substituted by lower alkylthio is, for example, 2-methylthio-ethoxy or 2-ethylthio-ethoxy, lower alkoxy substituted by lower alkanoylamino is, for example, 2-acetylamino-ethoxy, and lower alkoxy substituted by lower alkoxycarbonylamino is, for example, 2-methoxycarbonylamino-ethoxy or 2-ethoxycarbonylamino-ethoxy.

Lower alkyl substituted by carboxyl, lower alkoxycarbonyl, carbamoyl, N-lower alkylcarbamoyl, N,N-di-lower alkylcarbamoyl or cyano is, for example, carboxymethyl, methoxycarbonylmethyl, ethoxycarbonylmethyl, 2-carboxyethyl, 2-methoxycarbonylethyl, 2-ethoxycarbonylethyl, carbamoylmethyl, 2-carbamoylethyl, N-methylcarbamoylmethyl, N-ethyl-carbamoylmethyl, 2-N-methylcarbamoylethyl, 2-N-ethylcarbamoylethyl, N,N-dimethylcarbamoylmethyl, N,N-diethylcarbamoylmethyl, 2-N,N-dimethylcarbamoylethyl, 2-N,N-diethylcarbamoylethyl, cyanomethyl or 2-cyanoethyl.

Lower alkylene as a substituent of an aryl group $Ar_1$ or $Ar_2$ is, for example, 1,3-propylene or 1,4-butylene, whilst lower alkenylene is, for example, 1,3-prop-1-enylene or 1,4-but-1-enylene. Such a radical forms, together with a phenyl radical Ar, an optionally substituted indanyl, 1,2,3,4-tetrahydronaphthyl or indenyl group, substituted via an aromatic ring carbon atom.

An aza-lower alkenylene radical is above all 1-aza-1,3-prop-2-enylene, which, for example, forms together with a phenyl radical Ar an optionally substituted indolyl group which is bonded to the oxygen atom via a ring carbon atom of the carbocyclic part.

Lower alkylidenedioxy is, for example, methylenedioxy or isopropylidenedioxy, whilst alkylenedioxy is, for example, 1,2-ethylenedioxy.

Lower alkylene Alk is above all 1,2-ethylene, 1,2- or 2,3-propylene, 2-methyl-2,3-propylene or 2,3-butylene, as well as 1,3-propylene, 1,3- or 2,4-butylene and also 1,4-butylene.

Lower alkylamino is, for example, methylamino or ethylamino, and di-lower alkylamino is, for example, dimethylamino, ethylmethylamino or diethylamino, whilst lower alkyleneamino contains in particular 5–8, preferably 5 or 6, ring atoms and is, for example, pyrrolidino or piperidino, oxa-lower alkyleneamino above all contains 6 ring atoms and is, for example, morpholino, and aza-lower alkyleneamino in particular contains 6–8, preferably 6, ring atoms and represents, for example, 4-lower alkyl-piperazino, such as 4-methylpiperazino or 4-ethylpiperazino.

Salts of compounds of the formula I are above all acid addition salts, and in particular pharmaceutically usable non-toxic acid addition salts with suitable inorganic acids, such as hydrochloric acid, hydrobromic acid, sulphuric acid or phosphoric acid, or with suitable organic aliphatic, cycloaliphatic, aromatic, araliphatic or heterocyclic carboxylic acids or sulphonic acids, such as formic acid, acetic acid, propionic acid, succinic acid, glycollic acid, lactic acid, malic acid, tartaric acid, citric acid, ascorbic acid, maleic acid, fumaric acid, pyruvic acid, benzoic acid, anthranilic acid, 4-hydroxybenzoic acid, salicylic acid, phenylacetic acid, embonic acid, methane-sulphonic acid, ethanesulphonic acid, hydroxyethanesulphonic acid, ethylensulphonic acid, 4-chlorobenzenesulphonic acid, toluenesulphonic acid, naphthalenesulphonic acid, sulphanilic acid or cyclohexylaminesulphonic acid. Because of the close relationships between the new compounds in the free form and in the form of their salts, the free compounds and the salts are where appropriate also to be understood to include, respectively, the corresponding salts or free compounds, with regard to general sense and intended use.

The new compounds exhibit valuable pharmacological properties, especially β-receptor-blocking, blood pressure-lowering and vasodilatory effects, as well as antagonistic effects against the vasoconstricting effect of noradrenaline, which can be demonstrated by means of corresponding pharmacological experiments. Thus, the new compounds show an inhibition of the isoproterenol tachycardia on isolated guinea-pig hearts in a concentration range of about 0.01 μg/ml to about 3 μg/ml and on narcotised cats when intravenously administered in a dosage range of about 0.01 mg/kg to about 3 mg/kg, and an inhibition of the isoproterenol vasodilation of narcotised cats, with perfusion of the femoral artery, when administered intravenously in a dosage range of about 0.1 mg/kg to about 10 mg/kg. The lower dosage range for achieving the inhibiting effect on isoproterenol tachycardia indicates a cardioselective effect, compared with the β-receptor-blocking effect on the blood vessels. When administered intravenously in a dosage range of about 0.1 mg/kg to about 10 mg/kg the new compounds also cause a lowering of the arterial blood pressure in narcotised cats and produce a vasodilatory effect in cats with perfusion of the femoral artery. Furthermore, in a concentration range of about 0.01 μg/ml to about 10 μg/ml, they inhibit the vasoconstricting effect of noradrenaline on the isolatedly perfused mesenteric artery of rats. The new compounds can therefore be used as adrenergic β-receptor blocking agents, for example in the treatment of arrhythmias and angina pectoris, and as blood pressure-lowering agents.

Another group of the new compounds, especially 1-[2-(5-carbamoyl-2-pyridyloxy)-ethylamino]-3-(4-hydroxy-phenoxy)2-propanol and 1-[2-(2-carbamoyl-phenoxy)-ethylamino]-3-(3-pyrazinyloxy)-2-propanol, in particular have an effect on adrenergic β-receptors. Thus they specifically stimulate cardiac β-receptors. In particular, they have a positively inotropic and chronotropic effect on isolated guinea-pig auricles in a concentration range of 0.03–10 μg/ml and on narcotised cats in a dosage range of 0.002 to 0.5 mg/kg, administered intravenously. However, in narcotised cats, at doses which have a marked positively inotropic and chronoytropic effect, these compounds produce only slight lowering, if any, of the arterial blood pressure, that is to say they specifically stimulate the cardiac β-receptors in comparison to the β-receptors in the blood vessels and in this respect qualitatively differ markedly from isoproterenol, which stimulates the β-receptors of the heart and of the blood vessels to approximately the same degree. The new compounds can thus be used as positively inotropic agents, especially for the treatment of insufficiency of the heart muscle, by themselves or in combination with other preparations such as, for example, cardiac glycosides. However, they can also be used as valuable intermediate products for the manufacture of other valuable compounds, especially of pharmaceutically active compounds.

The invention in particular relates to compounds of the formula I, as well as acid addition salts, especially pharmaceutically usable acid addition salts, thereof, wherein $Ar_1$ denotes phenyl, lower alkylphenyl, such as 2-lower alkyl-phenyl, for example methylphenyl, such as 2-methylphenyl, lower alkenylphenyl, for example 2-lower alkenylphenyl, such as allylphenyl, for example 2-allylphenyl, oxa-lower alkyl-phenyl, for example 4-(oxa-lower alkyl)-phenyl, such as (2-methoxyethyl)-phenyl, for example (2-methoxyethyl)-phenyl, thia-lower alkylphenyl, for example 4-(thia-lower alkyl)-phenyl, such as (2-methylthioethyl)-phenyl, for example 4-(2-methylthioethyl)-phenyl, lower alkanoylamino-lower alkyl-phenyl, for example 4-(lower alkanoylamino-lower alkyl)-phenyl, such as (2-acetylaminoethyl)-phenyl, for example 4-(2-acetylaminoethyl)-phenyl, lower alkoxycarbonylamino-lower alkylphenyl, for example 4-(lower alkoxycarbonylamino-lower alkyl)-phenyl, such as (4-methoxycarbonylaminomethyl)-phenyl or 4-(2-methoxycarbonylaminoethyl)-phenyl, hydroxyphenyl, for example 4-hydroxyphenyl, lower alkoxyphenyl, for example 2-lower alkoxyphenyl, such as methoxyphenyl, for example 2-methoxyphenyl, lower alkenyloxyphenyl, for example 2-lower alkenyloxyphenyl, such as allyloxyphenyl, for example 2-allyloxyphenyl, oxa-lower alkoxyphenyl, for example 4-(oxa-lower alkoxy)-phenyl, such as (2-methoxyethoxy)-phenyl, for example 4-(2-methoxyethoxy)-phenyl, thia-lower alkoxyphenyl, for example 4-(thia-lower alkoxy)-phenyl, such as (2-methyl-thioethoxy)-phenyl, for example 4-(2-methylthioethoxy)-phenyl, halogenophenyl, such as chlorophenyl or bromophenyl, for example 2-chlorophenyl or 2-bromophenyl, lower alkanoyl-aminophenyl, for example 4-lower alkanoylaminophenyl, such as acetylaminophenyl, for example 4-acetylaminophenyl, lower alkoxycarbonylaminophenyl, for example 4-(lower alkoxycarbonylamino)-phenyl, such as methoxycarbonylaminophenyl, for example 4-methoxycarbonylaminophenyl, ureidophenyl, for example 4-methoxycarbonylaminophenyl, ureidophenyl, for example 4-ureidophenyl, N'-lower alkylureidophenyl, for example 4-N'-lower alkylureidophenyl, such as N'-methyl-ureidophenyl, for example 4-N'-methylureidophenyl, N',N'-di-lower alkylureidophenyl, for example 4-N',N'-di-lower alkylureidophenyl, such as N',N'-dimethylureidophenyl, for example 4-N',N'-dimethylureidophenyl, carbamoylphenyl, for example 4-carbamoylphenyl, N-lower alkylcarbamoylphenyl, for example 4-(N-lower alkylcarbamoyl)-phenyl, such as N-methyl-carbamoylphenyl, for example 4-N-methylcarbamoylphenyl, N,N-di-lower alkylcarbamoylphenyl, for example 4-(N,N-di-lower alkylcarbamoyl)-phenyl, such as N,N-dimethylcarbamoylphenyl, for example 4-N,N-dimethylcarbamoylpheny, cyanophenyl, for example 2- or 3-cyanophenyl, benzindanyl, for example 4-indanyl, or benz-indolyl, for example 4-indolyl, Alk represents lower alkylene with up to 4 carbon atoms and separates the nitrogen atom from the oxygen atom by two to three carbon atoms, and $Ar_2$ denotes pyridyl, for example 2-, 3- or 4-pyridyl, pyrimidinyl, for example 2- or 4-pyrimidinyl, or pyrazinyl, for example 2-pyrazinyl, or preferably denotes substituted pyridyl, pyrimidinyl or pyrazinyl, substituents being lower alkyl, for example methyl, lower alkanoylamino-lower alkyl, for example acetylaminomethyl, lower alkoxycarbonylamino-lower alkyl, for example methoxycarbonylaminomethyl, lower alkoxycarbonyl-lower alkyl, for example methoxycarbonylmethyl, carbamoyl-lower alkyl, for example carbamoylmethyl, N-lower alkylcarbamoyl-lower alkyl, for example N-methylcarbamoylmethyl, N,N-di-lower alkylcarbamoyl-lower alkyl, for example N,N-dimethylcarbamoylmethyl, cyanolower alkyl, for example cyanomethyl, hydroxyl, lower alkanoylamino, for example acetylamino, lower alkoxycarbonylamino, for example methoxycarbonylamino, lower alkoxycarbonyl, for example methoxycarbonyl, carbamoyl, N-lower alkylcarbamoyl, for example N-methylcarbamoyl, N,N-di-lower alkylcarbamoyl, for example N,N-dimethylcarbamoyl, or cyano, and the radical $Ar_2$ above all denotes pyridyl, for example 2-, 3- or 4-pyridyl, or pyrazinyl, for example 2-pyrazinyl, lower alkyl-pyridyl or -pyrazinyl, such as methylpyridyl or methyl-pyrazinyl, for example 3-methyl-2-pyridyl, 2-methyl-3-pyrazinyl or 2-methyl-6-pyrazinyl, lower alkanoylamino-lower alkyl-pyridyl or -pyrazinyl, such as acetylaminomethylpyridyl or -pyrazinyl, lower alkoxycarbonylamino-lower alkyl-pyridyl or -pyrazinyl, such as methoxycarbonylaminomethyl- or ethoxycarbonylaminomethyl-pyridyl or -pyrazinyl, carbamoyl-lower alkyl-pyridyl or -pyrazinyl, for example carbamoylmethyl-pyridyl or -pyrazinyl, (N-lower alkylcarbamoyl-lower alkyl)-pyridyl or -pyrazinyl, for example methylcarbamoyl-methyl-pyridyl or -pyrazinyl, (N,N-di-lower alkylcarbamoyl-lower alkyl)-pyridyl or -pyrazinyl, for example (N,N-di-methylcarbamoylmethyl)-pyridyl or -pyrazinyl, cyano-lower alkyl-pyridyl or -pyrazinyl, for example cyanomethyl-pyridyl or -pyrazinyl, hydroxypyridyl or hydroxypyrazinyl, lower alkanoylamino-pyridyl or -pyrazinyl, for example acetyl-aminopyridyl or acetylaminopyrazinyl, lower alkoxycarbonyl-pyridyl or -pyrazinyl, such as methoxycarbonyl-pyridyl or -pyrazinyl, carbamoyl-pyridyl or -pyrazinyl, for example 2-carbamoyl-3-pyridyl, 3-carbamoyl-2-pyridyl, 5-carbamoyl-2-pyridyl or 2-carbamoyl-6-pyrazinyl, N-lower alkylcarbamoylpyridyl or -pyrazinyl, for example 2-N-methylcarbamoyl-3-pyridyl, N,N-di-lower alkylcarbamoyl-pyridyl or -pyrazinyl, for example 3-N,N-dimethylcarbamoyl-2-pyridyl, or cyanopyridyl or cyanopyrazinyl, for example 3-cyano-2-pyridyl. This group of compounds exhibits particularly pronounced pharmacological properties.

The invention in particular relates to compounds of the formula

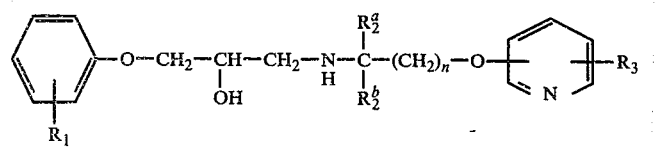

wherein $R_1$ denotes lower alkyl, especially methyl, lower alkenyl, for example allyl, hydroxyl, lower alkoxy, for example methoxy or ethoxy, lower alkenyloxy, for example allyloxy, halogen, for example chlorine, carbamoyl, lower alkylcarbamoyl, for example methylcarbamoyl, lower alkanoylamino, for example acetylamino, or lower alkoxycarbonylamino-lower alkyl, for example methoxycarbonylaminomethyl, each of the radicals $R_2^a$ and $R_2^b$ denotes hydrogen or methyl, $R_3$ denotes carbamoyl or lower alkylcarbamoyl, for example methylcarbamoyl, and $n$ denotes 1 or 2, and above all compounds of the formula (Iaa), wherein $R_1$ denotes lower alkyl, especially methyl (preferably in the 2-position), each of the radicals $R_1^a$ and $R_1^b$ denotes hydrogen or methyl, $R_3$ denotes carbamoyl and $n$ denotes 1, as well as acid addition salts, especially pharmaceutically usable non-toxic acid addition salts, of such compounds. This group of compounds exhibits particularly pronounced pharmacological properties.

The invention furthermore in particular relates to compounds of the formula I, as well as salts, above all acid addition salts, in particular pharmaceutically usable acid addition salts, thereof, wherein $Ar_2$ denotes pyridyl, for example 2-, 3- or 4-pyridyl, pyridazinyl, for example 3-pyridazinyl, pyrimidinyl, for example 2- or 4-pyrimidinyl, or pyrazinyl, for example 2-pyrazinyl, and these heterocyclic radicals can be monosubstituted, disubstituted or polysubstituted (the substituents being identical or different in the case of polysubstitution) by lower alkyl, for example methyl or ethyl, amino-lower alkyl, for example aminomethyl or 2-aminoethyl, lower alkanoylamino-lower alkyl, for example acetylaminomethyl, propionylaminomethyl, 2-acetyl-aminoethyl or 2-propionylaminoethyl, lower alkoxycarbonyl-amino-lower alkyl, for example methoxycarbonylaminomethyl, ethoxycarbonylaminomethyl, 2-methoxycarbonylaminoethyl or 2-ethoxycarbonylaminoethyl, hydroxy-lower alkyl, for example hydroxymethyl or 2-hydroxyethyl, lower alkoxy-lower alkyl, for example methoxyethyl, 2-methoxyethyl or 2-ethoxyethyl, lower alkylthio-lower alkyl, for example methylthiomethyl or 2-methylthioethyl, hydroxyl, lower alkoxy, for example methoxy or ethoxy, lower alkenyloxy, for example allyloxy, lower alkoxy-lower alkoxy, for example 2-methoxyethoxy, lower alkylthio, for example methylthio or ethylthio, halogen, for example chlorine or bromine, nitro, lower alkyl-amino, for example methylamino, ethylamino or isopropylamino, di-lower alkylamino, for example dimethylamino or diethylamino, lower alkyleneamino with 5–6 ring atoms, for example pyrrolidino or piperidino, oxa-lower alkyleneamino with 6 ring atoms, for example morpholino, or aza-lower alkenylene-amino with 6 rings atoms, wherein the aza nitrogen atom can optionally be substituted by lower alkyl, such as 4-lower alkyl-piperazino, for example 4-methyl-piperazino, lower alkanoylamino, for example acetylamino or propionylamino, lower alkoxycarbonylamino, for example methoxycarbonylamino or ethoxycarbonylamino, carboxyl, lower alkoxycarbonyl, for example methoxycarbonyl or ethoxycarbony, carbamoyl, N-lower alkylcarbamoyl, for example N-methylcarbamoyl or N-ethylcarbamoyl, N,N-di-lower alkyl-carbamoyl, for example N,N-dimethylcarbamoyl or N,N-diethylcarbamoyl, or cyano, Alk represents lower alkylene with up to 4 carbon atoms and separates the nitrogen atom from the oxygen atom by two to three carbon atoms, and $Ar_1$ denotes phenyl, pyridyl, for example 2-, 3- or 4-pyridyl, pyrimidinyl, for example 2- or 4-pyrimidinyl, or pyrazinyl, for example 2-pyrazinyl, or preferably substituted phenyl, pyridyl, pyrimidinyl or pyrazinyl, substituents being lower alkyl, for example methyl, lower alkanoylamino-lower alkyl, for example acetyl-aminomethyl, lower alkoxycarbonylamino-lower alkyl, for example methoxycarbonylaminomethyl, lower alkoxycarbonyl-lower alkyl, for example methoxycarbonylmethyl, carbamoyl-lower alkyl, for example carbamoylmethyl, N-lower alkylcarbamoyl-lower alkyl, for example N-methylcarbamoylmethyl, N,N-di-lower alkyl-carbamoyl-lower alkyl, for example N,N-dimethylcarbamoylmethyl, cyano-lower alkyl, for example cyanomethyl, hydroxyl, lower alkanoylamino, for example acetylamino, lower alkoxycarbonylamino, for example methoxycarbonylamino, lower alkoxycarbonyl, for example methoxycarbonyl, carbamoyl, N-lower alkyl-carbamoyl, for example N-methyl-carbamoyl, N,N-di-lower alkyl-carbamoyl, for example N,N-dimethylcarbamoyl, or cyano.

In the abovementioned preferred compounds, the radical $Ar_2$ in particular denotes pyridyl, for example 2-, 3- or 4-pyridyl, pyrimindinyl, for example 2- or 4-pyrimidinyl, or pyrazinyl, for example 2-pyrazinyl, lower alkyl-pyridyl, -pyrimidinyl or -pyrazinyl, for example 3-methyl-2-pyridyl, 4-methyl-2-pyridyl, 5-methyl-2-pyridyl, 6-methyl-2-pyridyl, 6-methyl-3-pyridyl, 2-methyl-4-pyridyl, 3-methyl-4-pyridyl, 2-ethyl-4-pyridyl, 4-methyl-2-pyrimidinyl, 4,6-dimethyl-2-pyrimidinyl, 6-methyl-4-pyrimidinyl, 5-ethyl-4-pyrimidinyl, 3-methyl-2-pyrazinyl or 6-methyl-2-pyrazinyl, amino-lower alkyl-pyridyl, -pyrimidinyl or -pyrazinyl, for example 5-aminomethyl-2-pyridyl or 5-(2-aminoethyl)-2-pyridyl, lower alkanoylamino-lower alkyl-pyridyl, -pyrimidinyl or -pyrazinyl, for example 5-acetylaminomethyl-2-pyridyl or 5-(2-acetyl-aminoethyl)-2-pyridyl, lower alkoxycarbonylamino-lower alkylpyridyl, -pyrimidinyl or -pyrazinyl, for example 5-methoxycarbonylaminomethyl-2-pyridyl, 5-(2-methoxycarbonylaminoethyl)-2-pyridyl or 5-(2-n-butoxycarbonylamino-ethyl)-2-pyridyl, hydroxy-lower alkyl-pyridyl, -pyrimidinyl or -pyrazinyl, for example 3-hydroxymethyl-2-pyridyl, lower alkoxy-lower alkyl-pyridyl, -pyrimidinyl or -pyrazinyl, for example 5-(2-methoxy-ethyl)-2-pyrimidinyl, lower alkylthio-lower alkyl-pyridyl, -pyrimidinyl or -pyrazinyl, for example 5-methylthiomethyl-2-pyrimidinyl, hydroxy-pyridyl, -pyrimidinyl or -pyrazinyl, for example 3-hydroxy-2-pyridyl or 6-hydroxy-2-pyridyl, hydroxy-lower alkyl-pyridyl, -pyrimidinyl or -pyrazinyl, for example 3-hydroxy-6-methyl 2-pyridyl, lower alkoxy-pyridyl, -pyrimidinyl or -pyrazinyl, for example 6-methoxy-2-pyridyl, 2-methoxy-3-pyridyl or 3-ethoxy-2-pyridyl, lower alkenyloxy-pyridyl, -pyrimidinyl or -pyrazinyl, for example 3-allyloxy-2-pyrazinyl, lower alkoxy-lower alkoxy-pyridyl, -pyrimidinyl or -pyrazinyl, for example 3-(2-methoxyethoxy)-2-pyrazinyl, lower alkylthio-pyridyl, -pyrimidinyl, or -pyrazinyl, for example 2-methylthio-4-pyrimidinyl or 3-ethylthio-2-pyrazinyl, halogeno-pyridyl, -pyrimidinyl or -pyrazinyl, for example 3-chloro-2-pyridyl, 5-chloro-2-pyridyl or 3-chloro-2-pyrazinyl, halogeno-lower alkyl-pyridyl, -pyrimidinyl or-pyrazinyl, for example 3-chloro-6-methyl-2-pyrazinyl, amino-lower alkyl-halogeno-pyridyl, -pyrimidinyl or-pyrazinyl, for example 5-(2-aminoethyl)-3-chloropyridyl, halogeno-lower alkoxycarbonylamino-lower alkyl-pyridyl, -pyrimidinyl or -pyrazinyl, for example 5-(2-ethoxycarbonylaminoethyl)-3-chloro-2-pyridyl, halogeno-hydroxy-lower alkyl-pyridyl, -pyrimidinyl or -pyridyl, for example 3-chloro-5-hydroxymethyl-pyridyl, nitro-pyridyl, -pyrimidinyl or -pyrazinyl, for example 5-nitro-2-pyridyl or 2-nitro-3-pyridyl, lower alkylamino-pyridyl, -pyrimidinyl or -pyrazinyl, for example 3-isopropylamino-2-pyrazinyl, di-lower alkylamino-pyridyl, -pyrimidinyl or -pyrazinyl, for example 3-dimethylamino-2-pyrazinyl, lower alkyleneaminopyridyl, -pyrimidinyl or -pyrazinyl, for example 2-pyrrolidino-3-pyridyl, morpholino-pyridyl, -pyrimidinyl or -pyrazinyl, for example 3-morpholino-2-pyrazinyl or 5-morpholino-2-pyrazinyl, (4-lower alkyl-piperazino)-pyridyl, -pyrimidinyl or -pyrazinyl, for example 3-(4-methylpiperazino)-2-pyrazinyl, halogeno-lower alkylamino-pyridyl, -pyrimidinyl or -pyrazinyl, for example 5-bromo-3-isopropyl-amino-2-pyrazinyl, halogeno-di-lower alkylamino-pyridyl, -pyrimidinyl or p-pyrazinyl, for example 5-bromo-3-dimethyl-amino-2-pyrazinyl, morpholino-lower alkyl-pyridyl, -pyrimidinyl or -pyrazinyl, for example 5-methyl-3-morpholino-2-pyrazinyl, halogeno-morpholino-pyridyl, -pyrimidinyl or -pyrazinyl, for example 5-bromo-3-morpholinopyrazinyl, lower alkanoylamino-pyridyl, -pyrimidinyl or -pyrazinyl, lower alkoxycarbonylamino-pyridyl, -pyrimidinyl or -pyrazinyl, lower alkoxycarbonyl-pyridyl, -pyrimidinyl or -pyrazinyl, di-lower alkylamino-lower alkoxycarbonyl-pyridy, -pyrimidinyl or -pyrazinyl, for example 5-ethoxycarbonyl-2-dimethylamino-4-pyrimidinyl, carbamoyl-pyridyl, -pyrimidinyl or -pyrazinyl, N-lower alkylcarbamoyl-pyridyl, -pyrimidinyl or -pyridazinyl, for example 5-N-methylcarbamoyl-2-pyridyl or 5-N-n-hexyl-carbamoyl-2-pyrimidinyl, halogeno-N-lower alkylcarbamoylpyridyl, -pyrimidinyl or -pyrazinyl, for example 3-chloro-5-N-methylcarbamoyl-2-pyridyl or 3-chloro-5-N-n-hexylcarbamoyl-2-pyridyl, or cyano-pyridyl, -pyrimidinyl or -pyrazinyl, for example 5-cyano-2-pyridyl, whilst the radical $Ar_1$ represents phenyl, pyridyl, for example 2-, 3- or 4-pyridyl, or pyrazinyl, for example 2-pyrazinyl, and especially substituted phenyl, pyridyl or pyrazinyl, such as lower alkyl-phenyl, -pyridyl or -pyrazinyl, for example 4-methyl-phenyl, 3-methyl-2-pyridyl, 2-methyl-3-pyrazinyl or 2-methyl-6-pyrazinyl, lower alkanoylamino-lower alkyl-phenyl, -pyridyl or -pyrazinyl, for example 4-(2-acetylaminoethyl)-phenyl, lower alkoxycarbonylamino-lower alkyl-phenyl, -pyridyl or -pyrazinyl, such as 2-methoxycarbonylaminomethyl-phenyl or 4-(2-methoxycarbonylaminoethyl)-phenyl, carbamoyl-lower alkyl-phenyl, -pyridyl or -pyrazinyl, for example 4-carbamoyl-methyl-phenyl, (N-lower alkylcarbamoyl-lower alkyl)-phenyl, -pyridyl or -pyrazinyl, for example 4-N-methylcarbamoylmethyl-phenyl, (N,N-di-lower alkylcarbamoyl-lower alkyl)-phenyl, -pyridyl or -pyrazinyl, for example 4-N,N-dimethyl-carbamoylmethyl-phenyl, cyano-lower alkyl-phenyl, -pyridyl or -pyrazinyl, hydroxy-phenyl, -pyridyl or -pyrazinyl, for example 4-hydroxyphenyl, lower alkanoylamino-phenyl, -pyridyl or -pyrazinyl, for example 4-acetylamino-phenyl, lower alkoxycarbonyl-phenyl, -pyridyl or -pyrazinyl, for example 2-methoxycarbonyl-phenyl, carbamoyl-phenyl, -pyridyl or -pyrazinyl, for example 2-carbamoyl-phenyl, 3-carbamoyl-phenyl, 4-carbamoyl-phenyl, 2-carbamoyl-3-pyridyl, 3-carbamoyl-2-pyridyl, 5-carbamoyl-2-pyridyl or 2-carbamoyl-3-pyrazinyl, N-lower alkyl-carbamoyl-phenyl, -pyridyl or -pyrazinyl, for example 4-N-methylcarbamoylphenyl or 2-N-methylcarbamoyl-3-pyridyl, N,N-di-lower alkyl-carbamoyl-phenyl, -pyridyl or -pyrazinyl, for example 3-N,N-dimethylcarbamoyl-2-pyridyl, or cyano-phenyl, -pyridyl or -pyrazinyl, for example 3-cyano-2-pyridyl, and Alk has the abovementioned preferred meaning. This group of compounds exhibits particularly pronounced pharmacological properties.

The invention relates in particular to compounds of the formula

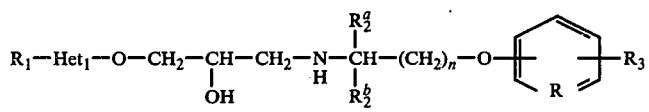

(Ibb)

wherein $Het_1$ represents a monocyclic, six-membered, monoazacyclic or diazacyclic radical of aromatic character, which is bonded to the oxygen atom via a ring carbon atom and in which $R_1$ substitutes a ring carbon atom, the two ring nitrogen atoms in a diazacyclic radical being separated by at least one ring carbon atom, $R_1$ represents hydrogen, lower alkyl, especially methyl, hydroxyl, lower alkoxy, for example methoxy or ethoxy, lower alkenyloxy, for example allyloxy, halogen, for example chlorine, carbamoyl, N-lower alkylcarbamoyl, for example methylcarbamoyl, lower alkanoylamino, for example acetylamino, or lower alkoxycarbonylamino-lower alkyl, for example methoxycarbonylaminomethyl, each of the groups $R_2^a$ and $R_2^b$ denotes hydrogen or methyl, R represents the radical of the formula $=CH-$ or of the formula $=N-$, $R_3$ is carbamoyl or N-lower alkyl-carbamoyl, for example methyl-carbamoyl and $n$ denotes 1 or 2, and above all compounds of the formula Ia, wherein $Het_1$ denotes pyridyl, especially 2-pyridyl, as well as 3- or 4-pyridyl, and also pyrimidinyl, especially 2- or 4-pyrimidinyl, or pyrazinyl, $R_1$ represents hydrogen or lower alkyl, especially methyl, each of the groups $R_2^a$ and $R_2^b$ in particular denote hydrogen as well as methyl, R represents the radical of the formula $=CH-$ or of the formula $=N-$, $R_3$ represents carbamoyl and $n$ represents 1, as well as acid addition salts, especially pharmaceutically usable non-toxic acid addition salts, of such compounds. These groups of compounds exhibit excellent pharmacological properties.

The new compounds of the present invention can be manufactured in a manner which is in itself known.

Thus they are obtained, for example, if, in a compound of the formula

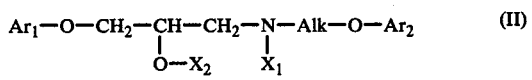

(II)

wherein at least one of the groups $X_1$ and $X_2$ denotes a group which is replaceable by hydrogen and the other represents hydrogen or a group which is replaceable by hydrogen, or $X_1$ and $X_2$ together represent a removable radical which is replaceable by two hydrogen atoms bonded to the oxygen atom and nitrogen atom respectively, or in a salt thereof, the radical $X_1$ and/or $X_2$ is replaced by hydrogen and, if desired, a resulting compound of the formula I is converted into another compound of the formula I and/or, if desired, a resulting free compound is converted into a salt or a resulting salt is converted into a free compound and/or, if desired, a resulting isomer mixture is separated into the individual isomers.

The groups $X_1$ and/or $X_2$ are split off by solvolysis or reduction. In the abovementioned starting materials of the formula II, $X_1$ is preferably a group replaceable by hydrogen, whilst $X_2$ above all represents hydrogen.

A particularly suitable removable group $X_1$ is above all a hydrogenolytically removable α-aryl-lower alkyl group, such as an optionally substituted 1-phenyl-lower alkyl group, wherein substituents, especially of the phenyl part, can be, for example, lower alkyl, such as methyl or tert.-butyl, hydroxyl, lower alkoxy, such as methoxy, halogen, for example chlorine or bromine and/or nitro, and above all $X_1$ is benzyl. A group $X_1$ can also represent a radical which is removable solvolytically, such as hydrolytically or acidolytically, or a radical which is removable reductively, including hydrogenolytically, especially a corresponding acyl radical, such as the acyl radical of an organic carboxylic acid, for example lower alkanoyl, such as acetyl, or aroyl, such as benzoyl, and also the acyl radical of a half-ester of carbonic acid, such as lower alkoxycarbonyl, for example methoxycarbonyl, ethoxycarbonyl or tert.-butoxycarbonyl, 2-halogeno-lower alkoxycarbonyl, for example 2,2,2-trichloro-ethoxycarbonyl or 2-iodoethoxycarbonyl, optionally substituted 1-phenyl-lower alkoxycarbonyl, for example benzyloxycarbonyl or diphenylmethoxycarbonyl, or aroylmethoxycarbonyl, for examle phenacyloxycarbonyl, or the acyl radical of an organic sulphonic acid, such as of an aromatic sulphonic acid, above all an optionally substituted phenylsulphonyl radical, wherein substituents have, for example, the meaning indicated for the above 1-phenyl-lower alkyl radical, and especially 4-methylphenylsulphonyl, and also an optionally substituted 1-polyphenyl-lower alkyl group, wherein substituents, above all of the phenyl part, have, for example, the abovementioned meaning, and above all trityl.

A group $X_2$ which is replaceable by hydrogen is preferably also a hydrogenolytically removable group, such as one of the abovementioned optionally substituted 1-phenyl-lower alkyl groups and above all benzyl. It can furthermore also be one of the solvolytically, including alcoholytically, or reductively removable acyl groups mentioned for the group $X_1$, or an aliphatic or araliphatic hydrocarbon radical which is polybranched at the linkage carbon atom and is optionally substituted, such as tert.-lower alkyl, for example tert.-butyl, or trityl.

A removable radical formed by $X_1$ and $X_2$ together is above all again a hydrogenolytically removable group, such as optionally substituted 1-phenyl-lower alkylidene, wherein substituents can be, for example, lower alkyl, such as tert.-butyl, hydroxyl, lower alkoxy, halogen and/or nitro, and especially benzylidene, as well as solvolytically, especially hydrolytically, removable groups, such as lower alkylidene, for example methylene or isopropylidene, or cycloalkylidene, for example cyclohexylidene. A further radical formed by the groups $X_1$ and $X_2$ together is the diacyl radical of carbonic acid or thiocarbonic acid, that is to say the carbonyl or thiocarbonyl group, respectively.

Starting materials usable in the form of salts are above all used in the form of acid addition salts, especially in the form of corresponding acids with inorganic acids, for example mineral acids, or of organic acids.

Hydrogenolytically removable radicals $X_1$ and/or $X_2$, especially optionally substituted 1-phenyl-lower alkyl groups, and also suitable acyl groups, such as optionally substituted 1-phenyl-lower alkoxycarbonyl, as well as optionally substituted 1-phenyl-lower alkylidene groups formed by the groups $X_1$ and $X_2$ together can be removed by treatment with catalytically activated hydrogen, for example with hydrogen in the presence of a nickel catalyst, such as Raney nickel, or of a suitable noble metal catalyst.

Hydrolytically removable groups $X_1$ and/or $X_2$, such as acyl radicals of organic carboxylic acids, for example lower alkanoyl, and of half-esters of carbonic acid, for example lower alkoxycarbonyl, and also, for example, trityl radicals, as well as lower alkylidene groups, or the carbonyl group, formed by the radicals $X_1$ and $X_2$ together, can, depending on the nature of such radicals, be removed by treatment with water under acid and/or basic conditions, for example in the presence of a mineral acid, such as hydrochloric acid or sulphuric acid, or of an alkali metal hydroxide or alkaline earth metal hydroxide or alkali metal carbonate or alkaline earth metal carbonate.

Acidolytically removable radicals are, in particular, certain acyl radicals of half-esters of carbonic acid, such as, for example, tert.-lower alkoxycarbonyl or optionally substituted diphenylmethoxycarbonyl radicals, and also tert.-lower alkyl radicals $X_2$; they can be removed by treatment with suitable strong organic carboxylic acids, such as lower alkanecarboxylic acids optionally substituted by halogen, especially fluorine, above all with trifluoroacetic acid (if necessary in the presence of an activating agent such as anisole), or with formic acid.

By reductively removable radicals $X_1$ and/or $X_2$ there are also understood groups which are removed on treatment with a chemical reducing agent (especially with a reducing metal or reducing metal compound). Such radicals are, in particular, 2-halogeno-lower alkoxycarbonyl or aroylmethoxycarbonyl, which can be removed, for example, on treatment with a reducing heavy metal, such as zinc, or with a reducing heavy metal salt, such as a chromium-II salt, for example chromium-II chloride or chromium-II acetate, usually in the presence of an organic carboxylic acid, such as formic acid or acetic acid, and of water. Reductively removable arylsulphonyl radicals, especially those which above all represent the radical $X_1$, can be replaced by hydrogen, for example on treatment with an alkali metal, for example lithium or sodium, in ammonia, or by means of electrolytic reduction.

The above reactions are carried out in a manner which is in itself known, usually in the presence of a solvent or solvent mixture, suitable reactants at the same time also being able to function as such solvents, and, if necessary, with cooling or warming, for example in a temperature range of about $-20°$ C. to about $+150°$ C., in an open or closed vessel and/or in the atmosphere of an inert gas, for example nitrogen.

The new compounds of the present invention can also be obtained when a compound of the formula

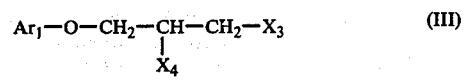

is reacted with a compound of the formula

wherein one of the groups $X_3$ and $X_5$ represents a reactive esterified hydroxyl group and the other represents the primary amino group, and $X_4$ represents the hydroxyl group, or wherein $X_3$ and $X_4$ together denote the epoxy group and $X_5$ represents the primary amino group, and, if desired, the additional process steps are carried out.

A reactive esterified hydroxyl group $X_3$ or $X_5$ is a hydroxyl group esterified by a strong acid, especially a strong inorganic acid, such as a hydrogen halide acid, especially hydrochloric acid, hydrobromic acid or hydriodic acid, or sulphuric acid, or by a strong organic acid, especially a strong organic sulphonic acid, such as an aliphatic or aromatic sulphonic acid, for example methane-sulphonic acid, 4-methylphenylsulphonic acid or 4-bromophenylsulphonic acid, and represents, above all, halogen, for example chlorine, bromine or iodine, or aliphatically or aromatically substituted sulphonyloxy, for example methylsulphonyloxy or 4-methylphenylsulphonyloxy.

The above reaction is carried out in a manner which is in itself known, advantageously (especially when using a starting material having a reactive esterified hydroxyl group) in the presence of a basic agent, such as an inorganic base, for example an alkali metal carbonate or hydroxide or alkaline earth metal carbonate or hydroxide, or of an organic basic agent, such as an alkali metal lower alkanolate, and/or an excess of the basic reactant, and usually in the presence of a solvent or solvent mixture and, if necessary, with cooling or warming, for example in a temperature range of about $-20°$ C. to about $+150°$ C., in an open or closed vessel and/or in an inert gas atmosphere, for example in a nitrogen atmosphere.

The new compounds can also be obtained by reacting a compound of the formula $Ar_1-OH$ (V) or a salt thereof with a compound of the formula

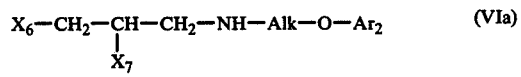

or with a corresponding azetidine compound of the formula

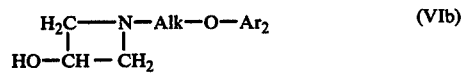

wherein $X_6$ represents a reactive esterified hydroxyl group and $X_7$ represents a hydroxyl group, or $X_6$ and $X_7$ together denote the epoxy group and, if desired, carrying out the additional process steps.

Salts of the phenolic starting material of the formula V are above all metal salts, especially alkali metal salts, for example sodium salts or potassium salts. A reactive esterified hydroxyl group has, for example, the above-mentioned meaning and above all represents halogen, for example chlorine or bromine.

The reaction of the starting materials of the formulae V and VIa or VIb with one another is carried out, for example, in the manner indicated above for the reaction of starting materials of the formula III with those of the formula IV, and when using the free phenolic starting material of the formula V the reaction is preferably carried out in the presence of an acid-binding basic condensation agent, such as an alkali metal hydroxide, for example sodium hydroxide or potassium hydroxide. Usually, the reaction is carried out in the presence of a solvent or solvent mixture and, if necessary, with cooling or warming, for example in a temperature range of about $-20°$ C. to about $+150°$ C., in an open or closed vessel and/or in an inert gas atmosphere, for example in a nitrogen atmosphere.

A further process modification of the manufacture of compounds of the formula I is that wherein, in a compound of the formula

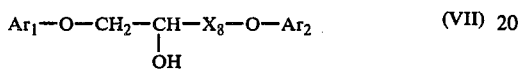

(VII)

wherein the grouping of the formula $-X_8-O-$ (VIIIa) is one of the radicals of the formulae $-CH=N-Alk-O-$ (VIIb), $-CH_2-N=Alk_1-O-$ (VIIc), $-C(=X_9)-NH-Alk-O-$ (VIId) or $-CH_2-NH-Alk_2-O-$ (VIIe), wherein $Alk_1$ represents the lower alkylenylidene radical corresponding to a radical Alk, and $Alk_2$ denotes the oxo- or thioxo-lower alkylene radical corresponding to a radical Alk, in which the carbon atom of the radical $Alk_2$ bonded to the nitrogen atom contains the oxo or thioxo group, and $X_9$ represents the oxo or thioxo group, the grouping of the formula $-X_8-O-$ is reduced to the radical of the formula $-CH_2-NH-Alk-O-$, and, if desired, the additional process steps are carried out.

The above reductive conversion of a radical of the formula $-X_8-O-$ (VIIa) to the desired grouping of the formula $-CH_2-NH-Alk-O-$ can be carried out in a manner which is in itself known, the choice of the suitable reducing agents depending of the nature of the groups of the formula VIIa. Light metal hydride reducing agents, such as alkali metal aluminium hydrides, for example lithium aluminium hydride (which are especially suitable for the reduction of carbamoyl groups), or alkali metal borohydrides, for example sodium borohydrides, as well as alkali metal cyanoborohydrides, for example sodium cyanoborohydride, or boron hydrides, for example diborane (which above all serve for the reduction of alkylideneamino groups), are particularly suitable for the reduction of groups of the formula VIIb and VIIc and of groups of the formula VIId and VIIe, wherein the radicals of the formula $-C(=X_9)-NH-$ and $-NH-Alk_2-$ contain a carbamoyl grouping. Furthermore, groupings of the formulae VIIb and VIIc can also be converted by treatment with catalytically activated hydrogen, such as, for example, with hydrogen in the presence of a heavy metal catalyst, for example Raney nickel, platinum oxide or palladium. Groupings of the formula VIId, wherein $X_9$ denotes a thiono group, and of the formula VIIe, wherein $Alk_2$ represents a thiono-lower alkyl radical, are converted to the grouping of the formula $-CH_2-NH-Alk-O-$ by reductive desulphurisation, for example by treatment with a hydrogenation catalyst, such as Raney nickel. The above reduction reactions are carried out in a manner which is in itself known, usually in the presence of an inert solvent and, if necessary, with cooling or warming, for example in a temperature range of about $-20°$ C. to about $+150°$ C., and/or in a closed vessel under pressure and/or in an inert gas atmosphere, for example a nitrogen atmosphere.

In choosing the suitable reactions, from those indicated above, for the preparation of compounds of the formula I, care must be taken that substituents which are present, above all of the radicals $Ar_1$ and/or $Ar_2$, are not converted or removed, if such conversions or removals are not desired. Thus, in particular, functionally modified carboxyl groups, such as esterified or amidised carboxyl groups, as well as cyano groups, present as substituents of the radicals $Ar_1$ and/or $Ar_2$, may participate in the reaction, and undergo conversion, during solvolyses, especially hydrolyses, and also during reductions. On the other hand, simultaneous conversions of substituents may be desired; for example, unsaturated substituents, such as lower alkenyl, can be reduced, for example to lower alkyl, under the conditions of a reduction process employed according to the invention.

Compounds obtained in accordance with the process can be converted, within the scope of the definition of the compounds of the formula I, into other end products in the usual manner, for example by modifying, introducing or removing suitable substituents.

Thus, unsaturated substituents, such as lower alkenyl, in resulting compounds can be reduced, for example by treatment with catalytically activated hydrogen.

Furthermore, the aromatic radical $Ar_1$ or $Ar_2$ in resulting compounds can be halogenated in the usual manner, for example chlorinated or brominated by treatment with chlorine or bromine, especially at room temperature or with cooling and in the presence of a catalyst, such as iodine, iron, iron-III chloride or iron-III bromide, aluminium chloride or aluminium bromide.

Furthermore, in resulting compounds with halogen-substituted radicals of aromatic character, the halogen can be replaced by hydrogen, for example by treatment with hydrogen in the presence of a customary hydrogenation catalyst, such as Raney nickel or palladium on charcoal.

Free carboxyl groups in the radicals $Ar_1$ or $Ar_2$ can be esterified in the usual manner, for example by reaction with a corresponding alcohol, advantageously in the presence of an acid, such as a mineral acid, for example sulphuric acid or hydrochloric acid, or in the presence of a water-binding agent, such as dicyclohexylcarbodiimide, or by reaction with a corresponding diazo compound, for example diazomethane. The esterification can also be carried out by reaction of a salt, preferably of an alkali metal salt, of the acid with a reactive esterified alcohol, for example a corresponding halide, such as a chloride.

Free carboxyl groups can be amidised in the usual manner, for example by reaction with ammonia, or with a primary or secondary amine, advantageously in the presence of a water-binding agent, such as dicyclohexylcarbodiimide, or by conversion of the carboxyl group into a halogenocarbonyl group, for example a chlorocarbonyl group, followed by reaction with ammonia or with a primary or secondary amine.

In compounds which contain an esterified carboxyl group, the latter can be converted into a free carboxyl group in the usual manner, for example by hydrolysis, preferably in the presence of strong bases, such as an alkali metal hydroxide, for example sodium hydroxide or potassium hydroxide, or strong acids, for example a strong mineral acid, such as a hydrogen halide acid, for example hydrochloric acid or sulphuric acid.

In compounds with an esterified carboxyl group as the substituent, this group can be converted into the corresponding carbamoyl group in the usual manner, for example by ammonolysis or aminolysis with ammonia or a primary or secondary amine.

Compounds with a carbamoyl group can be dehydrated to the corresponding cyano compounds in the usual manner, for example by the action of dehydrating agents, such as phosphorus pentoxide or phosphorus oxychloride, preferably at elevated temperatures.

Compounds which contain a cyano substituent can be saponified in the usual manner, for example in the presence of concentrated aqueous mineral acids or alkali metal hydroxides, to the corresponding carbamoyl compounds or directly to the carboxyl compounds.

Compounds with a cyano group as a substituent can be alcoholised in the usual manner, for example by addition of alcohols in the presence of an anhydrous acid, such as hydrogen chloride, and subsequent hydrolysis of the resulting imido-ester, to the corresponding compounds having esterified carboxyl groups.

As in the manufacturing processes, care must also be taken in carrying out the additional steps, to ensure that undesired side-reactions, which can result in the conversion of additional groupings, do not occur.

The reactions described above can, as appropriate, be carried out simultaneously or successively, and furthermore in optional sequence. If necessary, they are carried out in the presence of diluents, condensation agents and/or catalytic agents, at lowered or elevated temperature, in a closed vessel under pressure and/or in an inert gas atmosphere.

Depending on the process conditions and starting materials, the new compounds are obtained in the free form or in the form of their salts, which is also encompassed by the invention, and the new compounds or salts thereof can also be in the form of hemihydrates or monohydrates, sesquihydrates or polyhydrates. Acid addition salts of the new compounds can be converted into the free compounds in a manner which is in itself known, for example by treatment with basic agents, such as alkali metal hydroxides, alkali metal carbonates or alkali metal bicarbonates or ion exchangers. On the other hand, resulting free bases can form acid addition salts with organic or inorganic acids, for example with the abovementioned acids and, to prepared such salts, in particular those acids which are suitable for forming pharmaceutically usable salts are employed.

These or other salts, especially acid addition salts of the new compounds, such as, for example, picrates or perchlorates, can also be used for purifying the free bases obtained, by converting the free bases into salts, isolating and purifying these, and again liberating the bases from the salts.

Depending on the choice of the starting materials and procedures, the new compounds can be in the form of optical antipodes or racemates or, if they contain at least two asymmetrical carbon atoms, also in the form of racemate mixtures.

Resulting racemate mixtures can be separated into the two stereoisomeric (diastereomeric) racemates on the basis of the physico-chemical differences of the diastereoisomers, in a known manner, for example by chromatography and/or fractional crystallisation.

Resulting racemates can be separated into the antipodes in accordance with methods which are in themselves known, for example by recrystallisation from an optically active solvent, by treatment with suitable micro-organisms or by reaction with an optically active substance, especially an optically active acid, which forms salts with the racemic compound, and separation of the salt mixture obtained in this manner, for example on the basis of different solubilities, into the diastereomeric salts from which the free antipodes can be liberated by treatment with suitable agents. Examples of particularly customary optically active acids are the D- and L-forms of tartaric acid, di-o-toluyltartaric acid, malic acid, mandelic acid, camphorsulphonic acid, glutamic acid, aspartic acid or quinic acid. Advantageously, the more active of the two antipodes is isolated.

The invention also relates to those embodiments of the process according to which a compound obtainable as an intermediate product at any stage of the process is used as the starting material and the missing process steps are carried out, or the process is discontinued at any stage, or in which a starting material is formed under the reaction conditions, or in which a reactant is present in the form of its salts, where appropriate.

Suitably, those starting materials are used for carrying out the reactions according to the invention which lead to the initially particularly mentioned groups of end products and particularly to the end products which have been specifically described or singled out.

The starting materials are known or can, if they are new, be obtained according to methods which are in themselves known.

Thus, compounds of the formula II can be obtained analogously to the process modifications described above, for example by treating a compound of the formula V or a salt thereof with a compound of the formula

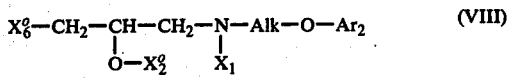

wherein $X_1$ has the abovementioned meaning and $X_2^o$ represents the group $X_2$, with at least one of the groups $X_1$ and $X_2^o$ being different from hydrogen, and $X_6^o$ denotes a reactive esterified hydroxyl group, or $X_2^o$ and $X_6^o$ together represent a carbon-oxygen bond or wherein $X_1$ and $X_2^o$ together represent a removable radical which is replaceable by two hydrogen atoms bonded to the oxygen atom or nitrogen atom and $X_6$ denotes a reactive esterified hydroxyl group, or by treating a compound of the formula

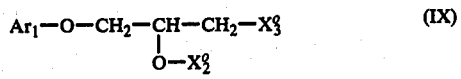

with a compound of the formula

wherein $X_2^o$ has the meaning given above for $X_2$, and one of the groups $X_3^o$ and $X_5^o$ represents a reactive esterified hydroxyl group and the other represents the group of the formula $-NH(X_1)$, wherein $X_1$ has the abovementioned meaning, with the proviso that at least one of the groups $X_1$ and $X_2$ becomes different from hydrogen, or wherein $X_2^o$ and $X_3^o$ form an oxygen-carbon bond and $X_5^o$ represents the group of the formula —NH($X_1$) and $X_1$ differs from hydrogen. The above reactions are carried out in a manner which is in itself known, for example as described above.

Starting materials of the formula III can be obtained, for example, by treating a compound of the formula V or a salt thereof with a compound of the formula

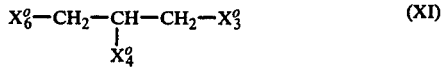 (XI)

wherein $X_6^o$ represents a reactive esterified hydroxyl group and $X_3^o$ and $X_4^o$ together denote the epoxy group and, if desired, by splitting open the epoxyethyl grouping in the resulting product to give a 2-amino-1-hydroxyethyl grouping or a 2-reactive esterified hydroxy-1-hydroxyethyl grouping. These reactions can be carried out in a manner which is in itself known.

Compounds of the formula IV can be obtained, for example, by treating a compound of the formula $X_{10}$—$Ar_2$ (X), wherein $X_{10}$ represents a suitable group which is removed, such as halogen, for example chlorine or bromine, nitro or lower alkylsulphonyl, for example methylsulphonyl, and which usually occupies the ortho- or para-position, relative to the ring nitrogen atom, in a heterocyclic radical $Ar_2$, with a compound of the formula $X_5^o$—Alk—OH (XI), wherein $X_5^o$ represents a suitably substituted amino group, for example amino substituted by one or two 1-aryl-lower alkyl, especially benzyl, or denotes a suitably etherified hydroxyl group, for example hydroxyl etherified by 1-aryl-lower alkyl, especially benzyl, or with a corresponding metal alcoholate, such as an alkali metal alcoholate, for example sodium alcoholate or potassium alcoholate, thereof, and/or in the presence of a suitable basic agent preferably capable of alcoholate formation, and liberating the amino or hydroxyl group, for example by treatment with catalytically activated hydrogen; in a resulting hydroxy intermediate product the hydroxyl group is converted to a reactive esterified hydroxyl group in a manner which is in itself known, for example by treatment with a thionyl halide, such as thionyl chloride, or with an organic sulphonyl halide, for example methylsulphonyl chloride or 4-methylphenylsulphonyl chloride. Starting materials of the formula IV, wherein the grouping of the formula $X_5$—Alk—O— in an azacyclic radical of the formula —$Ar_2$ occupies a meta-position relative to a ring nitrogen atom can be obtained, for example, by reacting a corresponding compound of the formula HO—$Ar_2$ (XII), or a metal compound, for example a sodium or potassium compound, thereof, with a compound of the formula $X_5^o$—Alk—Hal (XIII), wherein Hal represents halogen, for example chlorine or bromine, and $X_5^o$ has the abovementioned meaning, and, as described above, converting the radical $X_5^o$ in a resulting intermediate product into the primary amino group or into the reactive esterified hydroxyl group. The above reactions are carried out in a manner which is in itself known.

Starting materials of the formula VI$a$ can be obtained, for example, by reacting a compound of the formula

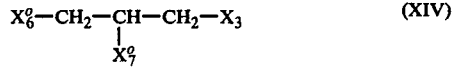 (XIV)

with a compound of the formula IV, wherein $X_3$ and $X_5$ have the abovementioned meanings, and $X_6^o$ and $X_7^o$ represent the groups $X_6$ or $X_7$ or groups which can easily be converted into the latter or appropriately protected groups and, if necessary, converting $R_6^o$ and/or $R_7^o$ in a resulting intermediate product into $R_6$ or $R_7$ respectively, if $R_6^o$ and/or $R_7^o$ differ from these. Further, starting materials of the formula VI$b$ can be obtained, for example, by converting the free hydroxyl groups in a 2-O-(1-aryl-lower alkyl)-glycerol compound, wherein 1-aryl-lower alkyl in particular represents benzyl, into corresponding reactive esterified hydroxyl groups, for example into halogen, such as chlorine, or bromine, and then reacting the product with a compound of the formula $H_2N$—Alk—O—$Ar_2$ (XV); in the intermediate product thus obtainable the 1-aryl-lower alkoxy group, especially the benzyloxy group, in the 3-position of the azetidine ring is split by treatment with catalytically activated hydrogen, and converted into the free hydroxyl group. The above reactions are carried out in a manner which is in itself known.

Starting materials of the formula VII can be obtained by reaction of amino compounds of the formula

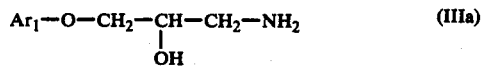 (IIIa)

wherein the hydroxyl group can optionally be present in a protected form, for example in an esterified or suitably etherified form, or of the formula

 (IVa)

with oxo compounds of the formula
 (XVIa)

wherein the divalent radical of the formula —($Alk_3$+λ H)— corresponds to the radical Alk, or of the formula

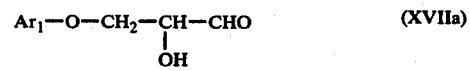 (XVIIa)

wherein the hydroxyl group can optionally be present in a protected form, for example in an esterified or suitably etherified form, or with suitable reactive derivatives, such as the halides, for example chlorides, of carboxylic acid compounds of the formula

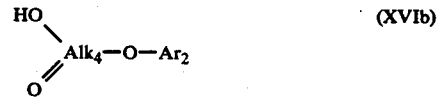 (XVIb)

wherein the divalent radical of the formula —($Alk_4$+2-H)— corresponds to the group Alk, or of the formula

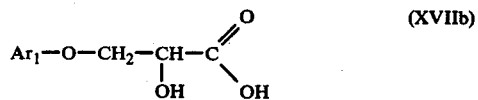 (XVIIb)

wherein the hydroxyl group can optionally be present in a protected form, for example in an esterified or suitably etherified form; in an intermediate product having a protected hydroxyl group, the latter is converted into the free form. The above reactions are carried out in a manner which is in itself known.

The new compounds can be used, for example, in the form of pharmaceutical preparations which contain a pharmacologically active amount of the active substance, if appropriate together with inorganic or organic, solid or liquid, pharmaceutically usable excipients which are suitable for enteral, for example oral, or parenteral administration. Thus, tablets or gelatine capsules are used, which contain the active compound together with diluents, for example lactose, dextrose, sucrose, mannitol, sorbitol, cellulose and/or glycine, and/or lubricants, for example silica, talc, stearic acid or salts thereof, such as magnesium stearate or calcium stearate and/or polyethylene glycol. Tablets can also contain binders, for example magnesium aluminium silicate, starches, such as maize starch, wheat starch, rice starch or arrowroot, gelatine, tragacanth, methylcellulose, sodium carboxymethylcellulose and/or polyvinylpyrrolidone, and, if desired, disintegrating agents, for example starches, agar, alginic acid or a salt thereof, such as sodium alginate, and/or effervescent mixtures, or adsorbents, dyestuffs, flavouring substances and sweeteners. Furthermore, the new pharmacologically active compounds can be used in the form of parenterally administrable preparations or of infusion solutions. Such solutions are preferably isotonic aqueous solutions or suspensions and these can be prepared before use, for example in the case of lyophilised preparations which contain the active substance by itself or together with an excipient, for example mannitol. The pharmaceutical preparations can be sterilised and/or contain auxiliaries, for example preservatives, stabilisers, wetting agents and/or emulsifiers, solubilising agents, salts for regulating the osmotic pressure and/or buffers. The present pharmaceutical preparations which can, if desired, contain further pharmacologically active compounds are prepared in a manner which is in itself known, for example by means of conventional mixing, granulating, dragee-making, dissolving or lyophilising processes, and contain from about 0.1% to 100%, especially from about 1% to about 50%, of lyophilisates with up to 100% of the active compound.

The dosage can depend on various factors, such as the method of administration, species, age and/or individual condition. The doses to be administered daily are, in the case of oral administration, between about 0.1 g and about 2.0 g for warm-blooded animals weighing about 70 kg.

The examples which follow serve to illustrate the invention.

EXAMPLE 1

A solution of 22.6 g of crude 1-{N-benzyl-N-[2-(5-carbamoyl-2-pyridyloxy)-ethyl]-amino}-3-(2-methyl-phenyloxy)-2-propanol in 230 ml of dioxane is hydrogenated in the presence of 2.3 g of a palladium-on-charcoal catalyst (5% strength) at 20°-30° C. and under atmospheric pressure, until an equimolar amount of hydrogen has been taken up. The catalyst is filtered off and the filtrate is evaporated under reduced pressure. The residue is recrystallised from ethyl methyl ketone and gives 1-[2-(5-carbamoyl-2-pyridyloxy)-ethylamino]-3-(2-methyl-phenyloxy)-2-propanol, melting point 139°-141° C.

The starting material can be obtained as follows:

(a) 51.4 g of a sodium hydride suspension (55% stength in paraffin oil) are added in portions, over the course of one hour, to a solution of 282 g of 2-N,N-dibenzylaminoethanol in 1,200 ml of dimethylformamide. The suspension is stirred for 2 hours at 40° C. and 92 g of 6-chloro-nicotinic acid amide are then added. The reaction mixture is stirred for 18 hours at 80° C. and evaporated under reduced pressure, and the residue is triturated with 2,000 ml of ethyl acetate. The insoluble residue is filtered off and the filtrate is evaporated under reduced pressure. The residue is crystallised from a mixture of diethyl ether and petroleum ether, giving 6-(2-N,N-dibenzylaminoethyloxy)-nicotinic acid amide of melting point 117°-121° C.

(b) A solution of 135 g of 6-(2-N,N-dibenzylaminoethyl-oxy)-nicotinic acid amide in 1,600 ml of ethanol is treated with an equimolar amount of hydrogen chloride (in the form of a solution in ethanol) and is hydrogenated, in the presence of 14 g of a 5% strength palladium-on-charcoal catalyst, at 20°-30° C. and under atmospheric pressure, until an equimolar amount of hydrogen has been taken up. The product which has crystallised out is dissolved by addition of water and warming; the catalyst is filtered off and the filtrate is evaporated under reduced pressure. The residue is dissolved in 2,500 ml of water and the 6-(2-N-benzylamino-ethyloxy)-nicotinic acid amide is precipitated by adding a concentrated aqueous sodium hydroxide solution; after recrystallisation from ethyl acetate, the product melts at 144°-145° C.

(c) 12.6 g of 6-(2-N-benzylamino-ethyloxy)-nicotinic acid amide are added to a solution of 17.6 g of 3-(2-methyl-phenyloxy)-1,2-epoxypropane in 150 ml of isopropanol and the mixture is heated to the boil under reflux, whereupon the initially suspended material dissolves. After 5 hours the solvent is evaporated under reduced pressure; the residue is dissolved in about 300 ml of diethyl ether and 15 ml of a 5 N solution of hydrogen chloride in methanol are added. The oily hydrochloride of 1-{N-benzyl-N-[2-(5-carbamoyl-2-pyridyloxy)-ethyl]-amino}-3-(2-methyl-phenyloxy)-2-propanol, which has been precipitated, is separated off, 20 ml of a concentrated aqueous sodium hydroxide solution are added thereto, and 1-{N-benzyl-N-[2-(5-carbamoyl-2-pyridyloxy)-ethyl]-amino}-3-(2-methyl-phenyloxy)-2-propanol is extracted with methylene chloride. The oily crude product obtainable after evaporation of the solvent is used without additional purification.

EXAMPLE 2

A solution of 25.9 g of crude 3-(2-allyl-phenyloxy)-1-{N-benzyl-N-[2-(5-carbamoyl-2-pyridyloxy)-ethyl]-amino}-2-propanol in 260 ml of methanol is hydrogenated in the presence of 3 g of a 5% strength palladium-on-charcoal catalyst at 20°-30° C. until two mol equivalents of hydrogen have been taken up. The catalyst is filtered off and the filtrate is evaporated under reduced pressure. 1-[2-(5-Carbamoyl-2-pyridyloxy)-ethylamino]-3-(2-n-propyl-phenyloxy)-2-propanol, thus obtainable, melts at 114°-118° C. and forms, with half the equivalent amount of fumaric acid, a neutral fumaric acid salt which after recrystallisation from a mixture of methanol and isopropanol melts at 168°-170° C.

(a) The starting material can be prepared analogously to the process described in Example 1 (c) by reaction of 3-(2-allyl-phenyloxy)-1,2-epoxypropane with 6-(2-N-benzylaminoethyloxy)-nicotinic acid amide. The oily 3-(2-allylphenoxy)-1-{N-benzyl-N-[2-(5-carbamoyl-2-pyridyloxy)-ethyl]-amino}-2-propanol is processed without additional purification.

EXAMPLE 3

A solution of 11.7 g of 1-{N-benzyl-N-[2-(3-carbamoyl-2-pyridyloxy)-ethyl]-amino}-3-(2-methyl-phenyloxy)-2-propanol in 120 ml of ethanol is hydrogenated in the presence of 1.2 g of a 5% strength palladium-on-charcoal catalyst at 20°–30° C. and under atmospheric pressure until the uptake of hydrogen ceases. The reaction product is worked up analogously to the process described in Example 1, giving crude 1-[2-(3-carbamoyl-2-pyridyloxy)-ethylamino]-3-(2-methyl-phenyloxy)-2-propanol. A solution of 1.5 g of fumaric acid in isopropanol is added thereto and the neutral fumaric acid salt of 1-[2-(3-carbamoyl-2-pyridyloxy)-ethylamino]-3-(2-methyl-phenyloxy)-2-propanol thus obtainable, is recrystallised from a mixture of isopropanol and water; melting point 156° C.

The starting material can be obtained as follows:

(a) Analogously to the process described in Example 1a), 185 g of 2-N,N-dibenzylamino-ethanol, 35.1 g of a 55% strength sodium hydride dispersion in paraffin oil and 60 g of 2-chloro-nicotinic acid amide give 2-(2-N,N-dibenzylamino-ethyloxy)-nicotinic acid amide, melting point 104°–106° C. 45 g thereof are hydrogenated in accordance with the process described in Example (1b), giving the hydrochloride of 2-(2-N-benzylamino-ethyloxy)-nicotinic acid amide, melting point 204°–206° C., which is converted into the free base, melting point 84°–86° C. 12.6 g of 2-(2-N-benzylamino-ethyloxy)-nicotinic acid amide are reacted with 17.6 g of 3-(2-methyl-phenyloxy)-1,2-epoxypropane in accordance with the process described in Example (1c), giving 1-{N-benzyl-N-[2-(3-carbamoyl-2-pyridyloxy)-ethyl]-amino}-3-(2-methyl-phenyloxy)-2-propanol, which melts at 109°–112° C. after recrystallisation from ethyl acetate.

EXAMPLE 4

A solution of 7.2 g of 1-{N-benzyl-N-[2-(2-carbamoyl-3-pyridyloxy)-ethyl]-amino}-3-(2-methyl-phenyloxy)-2-propanol in 80 ml of methanol is hydrogenated in the presence of one mol equivalent of hydrogen chloride and 0.7 g of a palladium-on-charcoal catalyst (5% strength) at room temperature and atmospheric pressure, until the hydrogen uptake ceases. Filtration and evaporation of the solution under reduced pressure gives the hydrochloride of 1-[2-(2-carbamoyl-3-pyridyloxy)-ethyl-amino]-3-(2-methyl-phenyloxy)-2-propanol, which melts at 181°–182° C. after recrystallisation from ethanol.

The starting material can be prepared as follows:

(a) 6.6 g of a sodium hydride suspension (55% strength in paraffin oil) are added in portions to a solution of 20.8 g of 3-hydroxy-2-pyridinecarboxylic acid amide in 200 ml of dimethylformamide at 0°–5° C., whilst stirring and cooling, and the mixture is stirred for one hour. Thereafter a solution of 32 g of 2-N,N-dibenzylamino-ethyl chloride in 150 ml of dimethylformamide is added dropwise over the course of 30 minutes, whilst continuing the cooling. The reaction mixture is stirred for 18 hours at 80° C. (bath temperature). The residue obtainable after evaporation under reduced pressure is treated with a solution of 6.3 g of fumaric acid in ethanol. The crystalline material which has precipitated is filtered off; the mother liquor is evaporated and the residue is chromatographed on 300 g of silica gel. Elution with a 99:1 mixture of benzene and methanol gives 3-(2-N,N-dibenzylamino-ethyloxy)-2-pyridinecarboxylic acid amide as an oily product, which is processed without additional purification.

(b) Catalytic debenzylation of 3-(2-N,N-dibenzylamino-ethyloxy)-2-pyridinecarboxylic acid amide analogously to the process described in Example 1 gives 3-(2-benzylamino-ethyloxy)-2-pyridinecarboxylic acid amide of melting point 110°–112° C.

(c) Reaction of 3-(2-N-benzylamino-ethyloxy)-2-pyridinecarboxylic acid amide with 3-(2-methyl-phenyloxy)-1,2-epoxy-propane gives, analogously to the process described in Example (1c), 1-{N-benzyl-N-[2-(2-carbamoyl-3-pyridyloxy)-ethyl]-amino}-3-(2-methyl-phenyloxy)-2-propanol as a reddish oil which is purified by chromatography on silica gel and elution with ethyl acetate.

EXAMPLE 5

A mixture of 13.2 g of crude 1-{N-benzyl-N-[2-(3-methyl-2-pyridyloxy)-ethyl]-amino}-3-(4-methylaminocarbonylphenyloxy)-2-propanol in 130 ml of ethanol, to which 1.3 g of a 5% strength palladium-on-charcoal catalyst have been added, is hydrogenated until the hydrogen uptake ceases. The oily residue obtained after filtration and evaporation of the solvent is dissolved in methanol, mixed with 1.77 g of fumaric acid and dissolved by warming; the solution is evaporated under reduced pressure. The oily residue which remains is crystallised from isopropanol and gives the neutral fumaric acid salt of 3-(4-methylaminocarbonyl-phenyloxy)-1-[2-(3-methyl-2pyridyloxy)-ethyl-amino]-2-propanol, melting point 173°–175° C.

The starting material can be prepared as follows:

(a) 8.0 g of a sodium hydride suspension (60% strength in paraffin oil) are added to a mixture of 31.7 g of 2-N-benzyl-amino-ethanol in 100 ml of dimethylformamide; the mixture is stirred for 2 hours at 40°–50° C. and 17.2 g of 2-bromo-3-methyl-pyridine are then added. The reaction mixture is stirred for 18 hours at 80° C., the solvent is evaporated off under reduced pressure and the residue is extracted with 300 ml of petroleum ether. The oily residue which remains after evaporation of the petroleum ether solution is distilled in a bulb tube; 2-(2-N-benzylamino-ethyloxy)-3-picoline, which boils at 120°–130° C. bath temperature and 0.05 mm Hg, is obtained as a mobile oil.

(b) A mixture of 6.3 g of 3-(4-methylaminocarbonyl-phenyloxy)-1,2-epoxy-propane, 7.4 g of 2-(2N-benzylaminoethyloxy)-3-picoline and 100 ml of isopropanol is heated for 20 hours under reflux and is then evaporated under reduced pressure. The residue is dissolved in 50 ml of 2 N hydrochloric acid, the solution is washed with 30 ml of diethyl ether and the acid aqueous phase is separated off, rendered alkaline with a concentrated aqueous sodium hydroxide solution and extracted with ethyl acetate. This gives crude 1-{N-benzyl-N-[2-(3-methyl-2-pyridyloxy)-ethyl]-amino}-3-(4-methylamino-carbonyl-phenyloxy)-2-propanol as an oily product which is processed further without purification.

EXAMPLE 6

4.8 g of crude 1-{N-benzyl-N-[3-(5-carbamoyl-2-pyridyloxy)-propyl]-amino}-3-(2-methyl-phenyloxy)-2-propanol are hydrogenated analogously to the process described in Example 1; the oily 1-[3-(5-carbamoyl-2-pyridyloxy)-propyl-amino]-3-(2-methyl-phenyloxy)-2-propanol thus obtainable melts at 109°–112° C. after crystallisation from ethyl acetate.

The starting material can be prepared as follows:

(a) A solution of 7 g of 3-N-benzylamino-propanol in 40 ml of dimethylformamide is reacted analogously to the process described in Example (1a) with 1.9 g of a sodium hydride suspension (55% strength in paraffin oil), and then with 5.5 g of 6-chloro-nicotinic acid amide. The crude 6-(3-N-benzylamino-propyloxy)-nicotinic acid amide thus obtainable is reacted with 4.9 g of 1,2-epoxy-3-(2-methyl-phenoxy)-propane; this gives 1-{N-benzyl-N-[3-(5-carbamoyl-2-pyridyloxy)-propyl]-amino}-3-(2-methyl-phenyloxy)-2-propanol, which is processed further without purification.

EXAMPLE 7

9.2 g of 3-(2-chloro-phenyloxy)-1,2-epoxy-propane are added to a solution of 9.0 g of 6-(2-aminoethoxy)-nicotinic acid amide in 200 ml of isopropanol and the mixture is heated under reflux for 4 hours. After evaporating off the solvent under reduced pressure, 1-[2-(5-carbamoyl-2-pyridyloxy)-ethyl-amino]-3-(2-chloro-phenoxy)-2-propanol is obtained; its hydrochloride melts at 202°-204° C. after recrystallisation from methanol.

The starting material can be prepared as follows:

(a) 36.1 g of 6-(2-N,N-dibenzylamino-ethyloxy)-nicotinic acid amide are hydrogenated analogously to the process described in Example (1b), but until two mol equivalents of hydrogen have been taken up. After filtration, and evaporation of the filtrate, 6-(2-aminoethyloxy)-nicotinic acid amide is obtained as the hydrochloride, from which the free base (melting point 154°-155° C. after recrystallisation from isopropanol) is obtainable by neutralisation with an equivalent amount of a concentrated aqueous sodium hydroxide solution.

EXAMPLE 8

A solution of 4.5 g of 1-amino-3-(2-methyl-phenyloxy)-2-propanol and 4.85 g of 3-(2-oxo-propyloxy)-2-pyridinecarboxylic acid amide in 100 ml of ethanol is heated under reflux for 3 hours. After cooling to room temperature, 1.9 g of sodium borohydride are added whilst stirring; the temperature gradually rises to 45° C. After the reaction has subsided, the mixture is stirred for a further hour. The reaction mixture is then acidified with 2 N hydrochloric acid whilst cooling, and is extracted with 20 ml of ethyl acetate. The aqueous phase is rendered alkaline with a concentrated aqueous sodium hydroxide solution and is extracted with three times 50 ml of ethyl acetate. After drying over sodium sulphate and evaporation of the organic solution, only, crude 1-[1-methyl-2-(2-carbamoyl-3-pyridyloxy)-ethyl-amino]-3-(2-methyl-phenyloxy)-2-propanol is obtained, which forms a neutral fumaric acid salt, melting point 145°-161° C. after recrystallisation from a mixture of methanol and ethyl methyl ketone.

The starting material can be prepared as follows:

(a) A mixture of 27.6 g of 3-hydroxy-2-pyridinecarboxylic acid amide and 31 g of potassium carbonate in 600 ml of acetonitrile is heated to the boil for two hours, whilst stirring well. 22.2 g of chloroacetone are added dropwise to the resulting thick paste in the course of 30 minutes. The reaction mixture is stirred for 20 hours whilst boiling under reflux. The undissolved material is filtered off after cooling and the filtrate is evaporated under reduced pressure. The residue is stirred with water, whereupon unconverted 3-hydroxy-2-pyridinecarboxylic acid amide remains as an undissolved residue. The aqueous solution is evaporated under reduced pressure and the residue is extracted with methylene chloride. Evaporation of the organic solution under reduced pressure gives crude 3-(2-oxo-propyloxy)-2-pyridinecarboxylic acid amide, which melts at 135°-140° C. after crystallisation from ethanol.

The following compounds can be obtained analogously if suitable starting materials are chosen: 1-[2-(3-ethoxy-2-pyridyloxy)-ethyl-amino]-3-(2-methyl-phenyloxy)-2-propanol; 1-[2-(6-chloro-2-pyridyloxy)-ethyl-amino]-3-(2-methyl-phenyloxy)-2-propanol; 1-[2-(3-acetylamino-2-pyridyloxy)-ethyl-amino]-3-(2-methyl-phenyloxy)-2-propanol; 1-[2-(5-carbamoyl-2-pyrimidinyloxy)-ethyl-amino]-3-(2-methyl-phenyloxy)-2-propanol; 1-[2-(3-methoxycarbonylaminomethyl-2-pyridyloxy)-ethylamino]-3-(2-methyl-phenyloxy)-2-propanol; 3-(2-methyl-phenyloxy)-1-[2-(5-methyl-2-pyrazinyloxy)-ethyl-amino]-2-propanol; 3-(2-methyl-phenyloxy)-1-[2-(3-methyl-2-pyrazinyloxy)-ethylamino]-2-propanol; 3-(2-methyl-phenyloxy)-1-[2-(2-pyrazinyloxy)-ethyl-amino]-2-propanol; 1-[2-(5-carbamoyl-2-pyridyloxy)-ethyl-amino]-3-(2-chloro-phenyloxy)-2-propanol; 1-[2-(5-carbamoyl-2-pyridyloxy)-ethyl-amino]-3-(4-methoxycarbonylaminomethyl-phenyloxy)-2-propanol; as well as their salts, especially their acid addition salts and above all the corresponding pharmaceutically usable salts.

EXAMPLE 9

A solution of 14.7 g of crude 6-(2-aminoethoxy)-picotinic acid N-methylamide in 150 ml of isopropanol is heated to the boil, whilst stirring, and a solution of 1-(2-methylphenoxy)-2,3-epoxy-propane in 50 ml of isopropanol is added dropwise thereto over the course of 5 hours. After boiling for a further 30 minutes under reflux, the solvent is evaporated off in vacuo. After some time, 3-(2-methyl-phenoxy)-1-[2-(5-methylcarbamoyl-2-pyridyloxy)-ethylamino]-2-propanol crystallises from the resulting residue; after recrystallisation from butanone, the compound melts at 105°-108° C. It forms a neutral fumarate of melting point 167°-170° C.

The starting material can be prepared as follows:

(a) 26.2 of crude 6-chloro-nicotinic acid chloride are introduced in portions into a solution of 25 ml of anhydrous methylamine in a mixture of 150 ml of dioxane and 50 ml of toluene whilst cooling at 0° C. to −5° C., and the mixture is then stirred for 3 hours longer, without further cooling. The reaction mixture is evaporated in vacuo, the residue is stirred with 100 ml of water and the undissolved material is filtered off and dried, giving crude 6-chloro-nicotinic acid N-methylamide of melting point 150°-154° C.

(b) 54 g of 2-N,N-dibenzylamino-ethanol are dissolved in 100 ml of dimethylformamide and 9.7 g of sodium hydride dispersion are added in portions, whilst stirring. After the evolution of gas has susbsided, the mixture is stirred for 2 hours at 40° C. After the addition of 19.0 g of 6-chloro-nicotinic acid N-methylamide the reaction temperature is raised to 80° C. and the reaction mixture is kept thereat for 16–18 hours. It is then evaporated in vacuo at 70° C./20 mm Hg, the residue is taken up in 300 ml of ethyl acetate, and the solution is washed with 100 ml of water, dried and again evaporated. Molecular path distillation at 140°-150° C./0.05 mm Hg removes the bulk of the excess 2-N,N-dibenzyl-aminoethanol. The residue is chromatographed on 500 g of silica gel (eluant:ether), giving crude 6-(2-N,N-dibenzylaminoethoxy)-nicotinic acid N-methylamide which melts at 79°–81° C. after crystallisation from ether/petroleum ether.

(c) A solution of 28.5 g of 6-(2-N,N-dibenzylaminoethoxy)-nicotinic acid N-methylamide in 300 ml of methanol is hydrogenated at 20°–30° C. and normal pressure, using a total of 6 g of palladium-on-charcoal catalyst (5% strength), which is added in 2 portions, until 2 mol equivalents of hydrogen have been taken up. After filtering off the catalyst and evaporating off the solvent, crude 6-(2-aminoethoxy)-nicotinic acid N-methylamide is obtained as a partially crystalline mass.

EXAMPLE 10

A solution of 23.6 g of 1-[N-benzyl-N-[2-(5-carbamoyl-2-pyridyloxy)-ethyl]-amino]-3-(4-benzyloxy-phenoxy)-2-propanol in 240 ml of methanol is hydrogenated with addition of 2.4 g of palladium-on-charcoal catalyst (5% strength) until 2 mol equivalents of hydrogen have been taken up. After evaporation, and recrystallisation from ethanol, 1-[2-(5-carbamoyl-2-pyridyloxy)-ethylamino]-3-(4-hydroxy-phenoxy)-2-propanol of melting point 148°–150° C. is obtained; this forms a neutral fumarate of melting point 198°–200° C.

(a) 1-[N-Benzyl-N-[2-(5-carbamoyl-2-pyridyloxy)-ethyl]-amino]-3-(4-benzyloxy-phenoxy)-2-propanol of melting point 115°–117° C., used as the starting material, is obtainable from 1-(4-benzyloxy-phenoxy)-2,3-epoxy-propane and 6-(2-benzylaminoethoxy)-nicotinic acid amide analogously to Example (1c).

EXAMPLE 11

A solution of 19.4 g of 1-[N-benzyl-N-[2-(5-carbamoyl-2-pyridyloxy)-ethyl]-amino]-3-phenoxy-2-propanol (melting point 86°–89° C.) in 200 ml of ethanol is hydrogenated analogously to Example 1, whereupon 1-[2-(5-carbamoyl-2-pyridyloxy)-ethylamino]-3-phenoxy-2-propanol of melting point 143°–144° C. is obtained. This forms a neutral fumarate of melting point 187°–189° C.

(a) The starting material is obtainable from 1,2-epoxy-3-phenoxy-propane and 6-(2-benzylamino-ethoxy)-nicotinic acid amide analogously to Example (1c).

EXAMPLE 12

A solution of 22 g of crude 1-[N-benzyl-N-[2-(5-carbamoyl-2-pyridyloxy)-1,1-dimethyl-ethyl]-amino]-3-(2-methyl-phenoxy)-2-propanol in 220 ml of methanol is hydrogenated analogously to Example 1, a total of 6 g of palladium-on-charcoal catalyst (5% strength) being added in 2 portions in order that the calculated amount of hydrogen should be taken up. Working up gives an oil from which 1-[2-(5-carbamoyl-2-pyridyloxy)-1,1-dimethyl-ethylamino]-3-(2-methyl-phenoxy)-2-propanol of melting point 122°–128° C. is obtained by crystallisation from ethyl acetate.

The starting material can be prepared as follows:

(a) A mixture of 106 g of benzaldehyde, 89 g of 2-amino-2-methyl-1-propanol, 2 ml of glacial acetic acid and 500 ml of benzene is heated for 3 hours under reflux, using a water separator. After completion of the reaction, the mixture is evaporated and the residue is dissolved in 2 liters of ethanol. After adding a total of 76 g of sodium borohydride in portions over the course of 2–3 hours, continuing to stir the mixture overnight at room temperature, and working up in the usual manner, 2-benzylamino-2-methyl-1-propanol is obtained, which melts at 50°–55° C. after crystallisation from ether.

(b) Reaction of 47 g of 2-benzylamino-2-methyl-1-propanol, 13.3 g of sodium hydride dispersion and 23.5 g of 6-chloronicotinic acid amide in 300 ml of dimethylformamide analogously to Example 1 a) gives 6-(2-benzylamino-2,2-dimethyl-ethoxy)-nicotinic acid amide of melting point 125°–126° C.

(c) A solution of 12 g of 6-(2-benzylamino-2,2-dimethyl-ethoxy)-nicotinic acid amide and 12 g of 1-(2-methylphenoxy)-2,3-epoxy-propane in 150 ml of isopropanol is boiled for 28 hours under reflux. After working up analogously to Example 1c), crude 1-[N-benzyl-N-[2-(5-carbamoyl-2-pyridyl-oxy)-1,1-dimethyl-ethyl]-amino]-3-(2-methyl-phenoxy)-2-propanol is obtained, which is used further without additional purification.

EXAMPLE 13

A solution of 17.3 g of 1-[N-benzyl-N-[2-(5-carbamoyl-2-pyridyloxy)-ethyl]-amino]-3-(2-methoxy-phenoxy)-2-propanol in 180 ml of ethanol is hydrogenated analogously to Example 1, giving 1-[2-(5-carbamoyl-2-pyridyloxy)-ethylamino]-3-(2-methoxy-phenoxy)-2-propanol, which melts at 132°–133° C. after crystallisation from ethanol. It forms a neutral fumarate as a hemihydrate which melts at 98°–105° C. after crystallisation from methanol.

(a) The starting material can be prepared analogously to Example 1c from 1-(2-methoxy-phenoxy)-2,3-epoxy-propane and 6-(2-benzyl-amino-ethoxy)-nicotinic acid amide; it melts at 108°–111° C. after crystallisation from ethyl acetate.

EXAMPLE 14

A solution of 4.0 g of 1-[N-benzyl-N-[(2-pyrimidinyloxy)-ethyl]-amino]-3-(2-methyl-phenyloxy)-2-propanol in 60 ml of methanol is hydrogenated with addition of 0.4 g of palladium-on-charcoal catalyst (5% strength) until one mol equivalent of hydrogen has been taken up. The catalyst is then filtered off and the solvent is evaporated off under reduced pressure. The oil which remains is dissolved in acetone and a solution of 1.0 g of oxalic acid in 10 ml of acetone is added, whereupon 1-[2-(2-pyrimidinyloxy)-ethylamino]-3-(2-methyl-phenyloxy)-2-propanol hydrogen oxalate is obtained as colorless crystals of melting point 148°–149° C.

The starting material can be obtained as follows:

(a) A solution of 96.5 g of 2-N,N-dibenzylaminoethanol in 200 ml of dimethoxyethane is added dropwise to a suspension of 9.6 g of sodium hydride in 100 ml of dimethoxyethane, whilst stirring at 25° C. After completion of the addition, the reaction mixture is stirred for 20 hours. A solution of 45.8 g of 2-chloropyrimidine in 200 ml of dimethoxyethane is then added dropwise at room temperature and thereafter the reaction mixture is heated to the boil for 4 hours, while stirring. After filtering off the sodium chloride which has separated out, and evaporating the solvent in vacuo, crude 2-(2-N,N-dibenzylaminoethoxy)-pyrimidine is obtained as a colourless oil, which is directly used further.

(b) A solution of 119.5 g of 2-(2-N,N-dibenzylaminoethoxy)-pyrimidine in 200 ml of ethanol is mixed with 188 ml of 2 N hydrochloric acid and hydrogenated, with addition of 12 g of palladium-on-charcoal catalyst (5% strength), until one mol equivalent of hydrogen has been taken up. After filtering off the catalyst, and evaporating the solvent under reduced pressure, an oil is obtained, which is treated with 100 ml of 10 N sodium hydroxide solution at 0° C. and extracted with benzene. The benzene extract is washed with saturated sodium chloride solution, dried over potassium carbonate, filtered and evaporated. Crude 2-(2-N-benzylaminoethoxy)-pyrimidine is obtained as a colourless oil, which is directly used further. The hydrogen-fumarate obtained by crystallisation from isopropanol melts at 131°–132° C.

(c) A solution of 4.1 g of 3-(2-methylphenoxy)-1,2-epoxy-propane and 5.75 g of 2-(2-N-benzylaminoethoxy)-pyrimidine in 50 ml of isopropanol is heated to 80° C. for 6 hours and the solvent is then evaporated under reduced pressure. The crude 1-[N-benzyl-N-[(2-pyrimidinyloxy)-ethyl]-amino]-3-(2-methyl-phenyloxy)-2-propanol which remains as an oil is directly used further.

EXAMPLE 15

A solution of 4.92 g of 1-(o-methyl-phenoxy)-2,3-epoxypropane and 4.59 g of 2-methyl-3-(2-amino-ethoxy)-pyrazine in 150 ml of isopropanol is stirred for 24 hours at about 20° C. and thereafter a further 1.47 g of 1-(o-methyl-phenoxy)-2,3-epoxy-propane are added. After standing for a further 24 hours at about 20° C., the reaction mixture is evaporated under a waterpump vacuum, the residue is dissolved in ether, the ether solution is extracted by shaking with 2 N hydrochloric acid and the combined hydrochloric acid extracts are rendered alkaline with sodium hydroxide solution and extracted by shaking with ether. The combined ether extracts are washed with water, dried over sodium sulphate and evaporated under a waterpump vacuum. The residue crystallises from methylene chloride/petroleum ether, giving 1-[2-(2-methyl-3-pyrazinyloxy)-ethyl-amino]-3-(2-methylphenoxy)-2-propanol; melting point 82°–84° C. The acid fumarate prepared with the calculated amount of fumaric acid crystallises from isopropanol, melting point 140°–141° C.

The starting material can be prepared as follows:

(a) 36.2 g of 2-N,N-dibenzylaminoethanol are dissolved in 375 ml of dimethylformamide and 6.6 g of a 55% strength suspension of sodium hydride in paraffin are added in portions at 0°–5° C., whilst stirring. When the evolution of hydrogen has ceased, 23.1 g of 2-methyl-3-chloropyrazine, dissolved in 75 ml of dimethylformamide, are added dropwise to the reaction mixture at 0°–5° C., whilst stirring. After completion of the addition, the mixture is slowly warmed to 80° C. and stirred at 80° C. for 15 hours. The reaction mixture is then cooled and poured onto 1 liter of ice water. The aqueous suspension is extracted by shaking with ether, the combined ether extracts are extracted by shaking with 2 N hydrochloric acid and the hydrochloric acid extracts are rendered alkaline with concentrated sodium hydroxide solution and extracted with ether. This ether extract is washed with water, dried over sodium sulphate and evaporated under a waterpump vacuum, giving 2-(N,N-dibenzylamino-ethoxy)-3-methylpyrazine, from which the hydrochloride is prepared by means of a solution of hydrochloric acid in ether, and is recrystallised from methanol/acetone; melting point 166°–178° C.

(b) A solution of 37.0 g of 2-(N,N-dibenzylamino-ethoxyl-3-methyl-pyrazine hydrochloride in 400 ml of methanol is hydrogenated under normal pressure, with addition of 4 g of palladium-on-charcoal catalyst (5% strength). After 28 hours, the calculated amount of hydrogen has been taken up. The reaction mixture is freed from the catalyst by filtration and evaporated under a waterpump vacuum, the residue is dissolved in methylene chloride and the solution is washed with 2 N sodium hydroxide solution and then with water, dried over sodium sulphate and evaporated under a waterpump vacuum. The residue is distilled in a bulb tube, giving 2-methyl-3-(2-aminoethoxy)-pyrazine as a colourless oil.

EXAMPLE 16

Analogously to Example 15, 4.59 g of 2-methyl-3-(2-amino-ethoxy)-pyrazine and 6.2 g of 1-(o-allyloxy-phenoxy)-2,3-epoxypropane give 1-[2-(2-methyl-3-pyrazinyloxy)-ethylamino]-3-(2-allyloxy-phenoxy)-2-propanol, which is recrystallised from ether; melting point 77°–80° C. The acid fumarate prepared therefrom with the calculated amount of fumaric acid crystallises from isopropanol/ether; melting point 108°–109° C.

EXAMPLE 17

Tablets containing 0.1 g of 1-[2-(5-carbamoyl-2-pyridyloxy)-ethyl-amino]-3-(2-methyl-phenyloxy)-2-propanol are prepared as follows:

| Composition (for 10,000 tablets): | |
|---|---|
| 1-[2-(5-Carbamoyl-2-pyridyloxy)-ethyl-amino]-3-(2-methyl-phenyloxy)-2-propanol | 1000.00 g |
| Lactose | 580.00 g |
| Maize starch | 750.00 g |
| Colloidal silica | 80.00 g |
| Talc | 80.00 g |
| Magnesium stearate | 10.00 g |
| Water, q.s. | |

The 1-[2-(5-carbamoyl-2-pyridyloxy)-ethyl-amino]-3-(2-methyl-phenyloxy)-2-propanol is mixed with the lactose, with a part of the maize starch and with colloidal silica and the mixture is forced through a sieve. A further part of the maize starch is worked to a paste with a five-fold amount of water on a waterbath and the powder mixture is kneaded with this paste until a slightly plastic mass is produced. This is forced through a sieve of about 3 mm mesh width and dried and the dry granules are again forced through a sieve. Thereafter, the remainder of the maize starch, the talc and the magnesium stearate are admixed and the resulting mixture is pressed to give tablets weighing 0.250 g (and having a breaking groove).

EXAMPLE 18

A suspension of 71.0 g of 1-amino-3-(3-methyl-2-pyridyloxy)-2-propanol hydrochloride, 79.5 g of 2-(2-bromoethoxy)-benzamide and 60 g of sodium bicarbonate in 700 ml of ethanol is heated to the boil under reflux for 18 hours whilst stirring. After adding a further 60 g of sodium bicarbonate and 30 g of 2-(2-bromoethoxy)-benzamide, the reaction mixture is again heated for 18 hours and is then filtered warm, and the filtrate is evaporated under reduced pressure. The oil which remains is dissolved in about 1,000 ml of ethyl acetate and the solution is washed with 100 ml of water and extracted with 2 N hydrochloric acid (total amount: 500 ml). The hydrochloric acid extracts are combined and rendered alkaline with a concentrated aqueous solution of sodium hydroxide, whilst cooling with ice. The oil which has precipitated is extracted with about 1,500 ml of ethyl acetate; the solvent is evaporated off under reduced pressure and the crystalline residue which remains is recrystallised from isopropanol. This gives 1-[2-(2-carbamoyl-phenyloxy)-ethyl-amino]-3-(3-methyl-2-pyridyloxy)-2-propanol of melting point 124°–125° C., which forms a neutral salt with fumaric acid, melting point 145°–146° C. after recrystallisation from methanol.

The starting material can be prepared as follows:

(a) 3-Benzyl-5-hydroxymethyl-2-phenyl-oxazolidine, used as the intermediate product (boiling point 168°–171° C./0.005 mm Hg) is obtained by reaction of glycerol glycid and benzylamine and treatment of the 3-benzylamino-1,2-propanediol thus obtainable (boiling point 160°–170° C./0.01 mm Hg) with benzaldehyde, whilst carrying out an azeotropic distillation with benzene.

(b) 32.1 g of a sodium hydride suspension (50% strength in paraffin oil) are added in portions to a solution of 224 g of 3-benzyl-5-hydroxymethyl-2-phenyl-oxazolidine in 670 ml of dimethylformamide, whilst keeping the temperature at 30° C. by cooling. After the addition, the reaction mixture is stirred for 2 hours at 40° C. internal temperature, 115 g of 2-bromo-3-methyl-pyridine are then added and the mixture is stirred for 20 hours at 80° C. internal temperature. The solvent is then evaporated off at 15 mm Hg and the residue is introduced into 500 ml of 2 N hydrochloric acid. The reaction mixture is stirred for two hours at 30° C. and left to stand for 16 hours. The aqueous solution is extracted with 100 ml of ethyl acetate and then rendered alkaline with 200 ml of a concentrated aqueous sodium hydroxide solution. The aqueous phase, containing the oil which separates out, is extracted with twice 500 ml of ethyl acetate and gives, after recrystallisation from ethyl acetate, 1-benzylamino-3-(3-methyl-2-pyridyloxy)-2-propanol, of melting point 83°–86° C.

(c) One mol equivalent of hydrogen chloride is added to a mixture of 100 g of 1-benzylamino-3-(3-methyl-2-pyridyloxy)-2-propanol in 2,500 ml of methanol and hydrogenation is then carried out in the presence of 40 g of a palladium-on-charcoal catalyst (5% strength) until one mol equivalent of hydrogen has been taken up (duration: about 45 hours), during which time the temperature has to be raised to about 50° C. After separating off the catalyst, evaporating the solution and recrystallising the residue from a mixture of methanol and ethyl acetate, the hydrochloride of 1-amino-3-(3-methyl-2-pyridyloxy)-2-propanol, melting point 134°–136° C., is obtained; the free base melts at 81°–83° C.

EXAMPLE 19

A suspension of 13.2 g of 1-amino-3-(3-methyl-2-pyridyloxy)-2-propanol hydrochloride, 14.5 g of 4-(2-bromo-ethoxy)-benzamide (melting point 172°–174° C.; prepared from 4-hydroxy-benzamide and 1,2-dibromoethane in acetonitrile in the presence of potassium carbonate) and 12 g of sodium bicarbonate in 150 ml of ethanol is stirred for 24 hours under reflux. The reaction mixture is worked up as described in Example 18 and gives a mixture of two oily bases which can be separated by crystallising the neutral salt with fumaric acid from a mixture of methanol and isopropanol. The material obtainable in a crystalline form is recrystallised from water and gives the neutral fumaric acid salt of 1-[2-(4-carbamoyl-phenyloxy)-ethyl-amino]-3-(3-methyl-2-pyridyloxy)-2-propanol, melting point -193°–195° C.

EXAMPLE 20

A mixture of 9.6 g of crude 1-{N-benzyl-N-[2-(4-carbamoyl-phenyloxy)-ethyl]-amino}-3-(3-methyl-2-pyridyl-oxy)-2-propanol, 1 mol equivalent of hydrogen chloride and 1 g of a palladium-on-charcoal catalyst (5% strength) in 100 ml of methanol is hydrogenated at about 30° C. and under atmospheric pressure until one mol equivalent of hydrogen has been taken up. The catalyst is filtered off, the filtrate is evaporated under reduced pressure and the oily residue is crystallised by adding about 20 ml of isopropanol. This gives the hydrochloride of 1-[2-(4-carbamoyl-phenyloxy)-ethyl-amino]-3-(3-methyl-2-pyridyloxy)-2-propanol, melting point 216°–217° C.; the free base is identical with the product described in Example 19.

The starting material can be prepared as follows:

(a) A suspension of 7.2 g of 1-benzylamino-3-(3-methyl-2-pyridyloxy)-2-propanol, 6.3 g of 4-(2-bromoethoxy)-benzamide and 5.5 g of sodium bicarbonate in 70 ml of dimethylformamide is stirred for 18 hours whilst warming to 100° C. internal temperature. After evaporation under a pressure of 10–15 mm Hg, a semi-solid mass remains, which is partitioned between 300 ml of ethyl acetate and 50 ml of water and worked up analogously to the process described in Example 18. This gives oily 1-{N-benzyl-N-[2-(4-carbamoyl-phenyloxy)-ethyl]-amino}-3-(3-methyl-2-pyridyloxy)-2-propanol, which is converted further without purification.

EXAMPLE 21

A solution of 16.0 g of 1-amino-3-(3-methyl-2-pyridyloxy)-2-propanol and 17.0 g of 1-(2-carbamoyl-phenyl-oxy)-acetone in 200 ml of benzene is heated under reflux, using a water separator, until the elimination of water has ceased after 2½ hours. Evaporation of the benzene gives a yellow oil containing 1-[2-(2-carbamoyl-phenyloxy)-1-methyl-ethylideneamino]-3-(3-methyl-2-pyridyloxy)-2-propanol, which is dissolved in 200 ml of absolute ethanol; 6.7 g of sodium borohydride are added in portions to the solution, whilst cooling with ice and stirring. The suspension is stirred for 16 hours at about 30° C. and evaporated under reduced pressure, and the residue is partitioned between 100 ml of a 2 N aqueous sodium hydroxide solution and 300 ml of ethyl acetate. The organic phase is washed with 50 ml of a saturated aqueous sodium chloride solution, dried over magnesium sulphate and evaporated. This gives a yellow oil which crystallises, from a mixture of benzene and diethyl ether, in the form of colourless crystals. The product is the diastereoisomer mixture of 1-[2-(2-carbamoyl-phenyloxy)-1-methyl-ethyl-amino]-3-(3-methyl-2-pyridyloxy)-2-propanol, melting point range 96°–110° C.

EXAMPLE 22

A solution of 11.0 g of 1-amino-3-(3-methyl-2-pyridyloxy)-2-propanol and 11.8 g of 3-(2-oxo-propyloxy)-2-pyridinecarboxylic acid amide in 200 ml of benzene is heated, with addition of 3–4 drops of glacial acetic acid, under a water separator until the elimination of water has ceased (duration: about 4 hours). The reduction of the 1-[2-(2-carbamoyl-3-pyridyloxy)-1-methyl-ethylidene-amino]-3-(3-methyl-2-pyridyloxy)-2-propanol, thus obtainable, with 4.6 g of sodium borohydride, and the working up of the reaction mixture is carried out analogously to the process described in Example 21. An oily material is obtained, which is reacted with 3.5 g of fumaric acid in ethanol and gives the crystalline diastereoisomer mixture of the neutral fumaric acid salt of 1-[2-(2-carbamoyl-3-pyridyloxy)-1-methyl-ethyl-amino]-3-(3-methyl-2-pyridyloxy)-2-propanol, melting range 151°–158° C.

The starting material can be prepared as follows:

(a) A mixture of 27.6 g of 3-hydroxy-2-pyridinecarboxylic acid amide and 31 g of potassium carbonate in 600 ml of acetonitrile is heated to the boil for 2 hours, while stirring well. 22.2 g of chloroacetone are added dropwise to the resulting thick paste in the course of 30 minutes. The reaction mixture is stirred for 20 hours whilst boiling under reflux. The undissolved material is filtered off after cooling and the filtrate is evaporated under reduced pressure. The residue is stirred with water, whereupon unconverted 3-hydroxy-2-pyridinecarboxylic acid amide remains as an undissolved residue. The aqueous solution is evaporated under reduced pressure and the residue is extracted with methylene chloride. The organic solution, after evaporation under reduced pressure, gives crude 3-(2-oxo-propoxy)-2-pyridinecarboxylic acid amide which melts at 135°–140° C. after crystallisation from ethanol.

EXAMPLE 23

A solution of 9.0 g of 4-(2-aminoethoxy)-benzamide in 120 ml of isopropanol is heated to the reflux temperature and a solution of 9.3 g of 2-chloro-3-(2,3-epoxy-propoxy)-pyrazine in 120 ml of isopropanol is added dropwise; duration of the addition: 5 hours. Thereafter the reaction mixture is heated to the reflux temperature for a further 7 hours. After completion of the reaction, the mixture is evaporated under a waterpump vacuum. The residue crystallises from ethyl acetate and gives 1-[2-(4-carbamoylphenyl-oxy)-ethyl-amino]-3-(2-chloro-3-pyrazinyloxy)-2-propanol, melting point 134°–135° C. after recrystallisation from isopropanol. The hydrochloride prepared therefrom using the calculated amount of methanolic hydrochloric acid melts at 223°–225° C. after crystallisation from a mixture of methanol and acetone.

The starting material can be prepared as follows:

(a) 9.6 g of sodium hydride are added in portions, whilst stirring, to a solution of 59.6 g of 2,3-dichloropyrazine and 52.8 g of 2,2-dimethyl-4-hydroxymethyl-1,3-dioxolane in 500 ml of hexamethylphosphoric acid triamide at 0°–5° C. (duration of the addition: 40 minutes). The reaction mixture is then stirred for 40 hours at room temperature after which it is poured onto an ice-water mixture. The aqueous phase is extracted with diethyl ether. The combined organic extracts are washed with water, dried over sodium sulphate and evaporated under a waterpump vacuum. 4-(2-Chloro-3-pyrazinyloxymethyl)-2,2-dimethyl-1,3-dioxolane is obtained as an oily residue.

(b) 320 ml of 1 N hydrochloric acid are added to a solution of 95 g of 4-(2-chloro-3-pyrazinyloxymethyl)-2,2-dimethyl-1,3-dioxolane in 1,000 ml of ethanol and the mixture is stirred for 15 hours at room temperature. It is then evaporated completely in a waterpump vacuum. The residue crystallises from a mixture of chloroform and diethyl ether. This gives 3-(2-chloro-3-pyrazinyloxy)-2-hydroxy-1-propanol, melting point 48°–50° C., which is purified by distillation in a high vacuum, boiling point 140°–145° C./0.01 mm Hg.

(c) A mixture of 71 g of 3-(2-chloro-3-pyrazinyloxy)-2-hydroxy-1-propanol, 350 ml of orthoacetic acid triethyl ester and 0.03 ml of trifluoroacetic acid is left to stand for 2 hours at room temperature. The reaction mixture is then evaporated completely under a waterpump vacuum. This gives 2-ethoxy-4-(2-chloro-3-pyrazinyloxymethyl)-2-methyl-1,3-dioxolane which is converted further without purification.

(d) A solution of 95 g of 2-ethoxy-4-(2-chloro-3-pyrazinyloxymethyl)-2-methyl-1,3-dioxolane in 700 ml of methylene chloride is treated dropwise, whilst stirring, with 38 g of trimethylchlorosilane (duration of the addition: 30 minutes), whilst keeping the temperature of the reaction mixture at about 25° C. by cooling. The reaction mixture is then stirred for 1 hour at room temperature after which it is evaporated completely under a waterpump vacuum. This gives 2-acetoxy-3-(2-chloro-3-pyrazinyloxy)-1-propyl chloride as an oily product which is converted further without purification.

(e) A solution of 11.9 g of tetrabutylammonium bisulphate in 400 ml of a 2 N aqueous sodium hydroxide solution is added to a solution of 87 g of 2-acetoxy-3-(2-chloro-3-pyrazinyloxy)-1-propyl chloride in 800 ml of methylene chloride, and the mixture is stirred thoroughly for 15 hours at room temperature. The organic phase is then separated off, washed with water until neutral, dried over sodium sulphate and evaporated under a waterpump vacuum. This gives 2-chloro-3-(2,3-epoxypropoxy)-pyrazine as an oily product which is used without additional purification.

EXAMPLE 24

Analogously to the process described in Example 23, 9.0 g of 2-(2-aminoethoxy)-benzamide and 9.3 g of 2-chloro-3-(2,3-epoxy-propoxy)-pyrazine give 1-[2-(2-carbamoyl-phenyloxy)-ethyl-amino]-3-(2-chloro-3-pyrazinyloxy)-2-propanol, melting point 132°–133° C. The neutral fumaric acid salt prepared therefrom using the calculated amount of fumaric acid crystallises from a mixture of methanol and diethyl ether, melting point 167°–168° C.

The following compounds can be prepared in the manner described above if suitable starting materials are selected: 1-[2-(3-carbamoyl-phenyloxy)-ethyl-amino]-3-(3-methyl-2-pyridyloxy)-2-propanol; 3-(3-ethoxy-2-pyridyloxy)-1-[2-(4-carbamoyl-phenyloxy)-ethyl-amino]-2-propanol; 1-[2-(4-acetylamino-phenyloxy)-ethyl-amino]-3-(3-methyl-2-pyridyl-oxy)-2-propanol; 1-[2-(4-carbamoyl-phenyloxy)-1,1-dimethyl-ethyl-amino]-3-(3-methyl-2-pyridyloxy)-2-propanol; 1-[2-(4-hydroxy-phenyloxy)-ethyl-amino]-3-(3-methyl-2-pyridyloxy)-2-propanol; 1-[2-(2-methoxycarbonylaminomethyl-phenyloxy)-ethyl-amino]-3-(3-methyl-2-pyridyloxy)-2-propanol; 1-[2-(4-carbamoyl-phenyloxy)-ethyl-amino]-3-(4-methyl-2-pyridyloxy)-2-propanol; 1-[2-(4-carbamoyl-phenyloxy)-ethyl-amino]-3-(5-chloro-2-pyridyloxy)-2-propanol; 1-[2-(4-carbamoyl-phenyloxy)-ethyl-amino]-3-(6-hydroxy-2-pyridyloxy)-2-propanol; 1-[2-(4-carbamoyl-phenyloxy)-ethyl-amino]-3-(2-pyrazinyloxy)-2-propanol; 1-[2-(2-carbamoyl-phenyloxy)-ethyl-amino]-3-(2-pyrazinyloxy)-2-propanol; 1-[2-(4-carbamoyl-phenyloxy)-ethyl-amino]-3-(3-methyl-2-pyrazinyloxy)-2-propanol and 1-[2-(2-carbamoyl-phenyloxy)-ethyl-amino]-3-(3-methyl-2-pyrazinyloxy)-2-propanol, as well as their salts, especially their acid addition salts and above all the corresponding pharmaceutically usable salts thereof.

EXAMPLE 25

A solution of 34.8 g of 1-[N-benzyl-N-[3-(2-carbamoylphenoxy)-propyl]-amino]-3-(3-methyl-2-pyridyloxy)-2-propanol hydrochloride in 350 ml of methanol is hydrogenated, with addition of 3.5 g of palladium-on-charcoal catalyst (5% strength), at 20°–30° C. and normal pressure, until 1 equivalent of hydrogen has been taken up.

After filtering off the catalyst and evaporating off the solvent, the residue is rendered alkaline with 2 N sodium hydroxide solution and the base is extracted with 300 ml of ethyl acetate. The crude crystalline base obtained after evaporating off the solvent is dissolved in methanol and 3.1 g of fumaric acid are added. After addition of ether, colourless 1-[3-(2-carbamoyl-phenyloxy)-propylamino]-3-(3-methyl-2-pyridyloxy)-2-propanol crystallises as the neutral fumarate of melting point 164°–165° C.

The starting material can be prepared as follows:

(a) 27.2 g of 1-benzylamino-3-(3-methyl-2-pyrimidyloxy)-2-propanol, 30.4 g of o-(3-bromopropoxy)-benzamide and 12.6 g of sodium bicarbonate in 300 ml of ethanol are boiled under reflux for 26–30 hours.

After working up analogously to Example 18, crude 1-[N-benzyl-N-[3-(2-carbamoyl-phenoxy)-propyl]-amino]-3-(3-methyl-2-pyridyloxy)-2-propanol is obtained as an oil of which the hydrochloride melts at 129°–132° C. after recrystallisation from isopropanol-/ethyl acetate.

EXAMPLE 26

A solution of 5.7 g of 1-[N-benzyl-N-[2-(4-carbamoyl-phenyloxy)-ethyl]-amino]-3-(2-pyrimidinyloxy)-2-propanol in 60 ml of ethanol is hydrogenated, with addition of 0.6 g of palladium-on-charcoal catalyst (5% strength), until one mol equivalent of hydrogen has been taken up. The catalyst is then filtered off and the solvent is largely evaporated in vacuo. After adding a solution of 1.2 g of oxalic acid in acetone, 1[2-(4-carbamoylphenyloxy)-ethyl-amino]-3-(2-pyrimidinyloxy)-2-propanol hydrogen-oxalate is obtained in colourless crystals of melting point 184°–186° C. (decomposition).

The starting material can be prepared as follows:

(a) A solution of 26.93 g of 3-benzyl-5-hydroxymethyl-2-phenyl-oxazolidine in 100 ml of dimethoxyethane is added dropwise to a suspension of 2.4 g of sodium hydride in 50 ml of dimethoxyethane, whilst keeping the temperature of the reaction mixing at 20° C. The mixture is then stirred for 7 hours, after which a solution of 11.45 g of 2-chloro-pyrimidine in 30 ml of dimethoxyethane is added dropwise at 20° C. After stirring for 20 hours and boiling under reflux, the solvent is distilled off under reduced pressure, the residue is warmed with 10 ml of concentrated hydrochloric acid and 30 ml of water to 60° C. and then cooled, and the mixture is extracted with ether. 15 ml of 10 N sodium hydroxide solution are added to the aqueous phase at 0° C., the mixture is then extracted with ethyl acetate and the organic phase is dried over sodium sulphate, filtered and evaporated in vacuo. The residue is dissolved in acetone and a solution of 9.0 g of oxalic acid in acetone is added. The hydrogen-oxalate of 1-benzylamino-3-(2-pyrimidinyloxy)-2-propanol, of melting point 188°–189° C., is obtained. From this, the free base is obtained as an oil by adding sodium hydroxide solution at 0° C., extracting with ethyl acetate, drying the organic phase over sodium sulphate, filtering and evaporating.

(b) Analogously to Example 18, a suspension of 15.7 g of 1-benzylamino-3-(2-pyrimidinyloxy)-2-propanol, 17.6 g of 2-(4-bromoethoxy)-benzamide and 7.7 g of sodium bicarbonate in 170 ml of ethanol is heated to the boil for 30 hours, whilst stirring. After cooling, the reaction mixture is filtered, the filtrate is evaporated under reduced pressure, the oil which remains is dissolved in methanol and hydrochloric acid in ether is added, after which 1-[N-benzyl-N-[2-(4-carbamoyl-phenyloxy)-ethyl]-amino]-3-(2-pyrimidinyloxy)-2-propanol hydrochloride of melting point 180°–181° C. is obtained. Addition of sodium hydroxide solution at 0° C., extraction with ethyl acetate, drying of the organic phase over sodium sulphate, filtration and evaporation gives the free base as an oil.

EXAMPLE 27

Analogously to Example 23, 9.0 g of 4-(2-aminoethoxy)-benzamide and 8.3 g of 2-methyl-3-(2,3-epoxy-propoxy)-pyrazine give 1-[2-(4-carbamoyl-phenoxy)-ethylamino]-3-(2-methyl-3-pyrazinyloxy)-2-propanol of melting point 105°–120° C. The neutral fumarate prepared therefrom with the calculated amount of fumaric acid is recrystallised from ethanol; melting point 176°–177° C.

The starting material can be prepared as follows:

(a) Analogously to Example (23a), 51.5 g of 2-chloro-3-methylpyrazine and 52.8 g of 2,2-dimethyl-4-hydroxy-methyl-1,3-dioxolane give 4-(2-methyl-3-pyrazinyloxymethyl)-2,2-dimethyl-1,3-dioxolane as an oily residue.

(b) Analogously to Example (23b), 82 g of 4-(2-methyl-3-pyrazinyloxymethyl)-2,2-dimethyl-1,3-dioxolane give 3-(2-methyl-3-pyrazinyloxy)-2-hydroxyl-1-propanol; melting point 77°–78° C.

(c) Analogously to Example (23c), 58.5 g of 3-(2-methyl-3-pyrazinyloxy)-2-hydroxy-1-propanol give 2-ethoxy-4-(2-methyl-3-pyrazinyloxymethyl)-2-methyl-1,3-dioxolane as an oily residue.

(d) Analogously to Example (23d), 89 g of 2-ethoxy-4-(2-methyl-3-pyrazinyloxymethyl)-2-methyl-1,3-dioxolane give 2-acetoxy-3-(2-methyl-3-pyrazinyloxy)-1-propyl chloride as an oily residue.

(e) Analogously to Example (23e), 85 g of 2-acetoxy-3-(2-methyl-3-pyrazinyloxy)-1-propyl chloride give 2-methyl-3-(2,3-epoxy-propoxy)-pyrazine as an oily residue.

EXAMPLE 28

Analogously to Example 23, 9.0 g of 2-(2-aminoethoxy)-benzamide and 9.3 g of 2-methyl-3-(2,3-epoxy-propoxy)-pyrazine give 1-[2-(2-carbamoylphenoxy)-ethylamino]-3-(2-methyl-3-pyrazinyloxy)-2-propanol; melting point 127°–128° C. The neutral fumarate prepared therefrom with the calculated amount of fumaric acid is recrystallised from methanol/ether; melting point 149° C.

EXAMPLE 29

A solution of 11.4 g of 1-[N-[2-(2-carbamoyl-phenoxy)-ethyl]-N-benzylamino]-3-(2-chloro-3-pyrazinyloxy)-2-propanol in 110 ml of methanol is hydrogenated, with addition of 1.1 g of palladium-on-charcoal catalyst (5% strength), at 20° C. and normal pressure. After 9 hours, the hydrogen uptake has ceased. The reaction mixture is freed from the catalyst by filtration and is evaporated in a water-pump vacuum, and the residue is taken up in ethyl acetate. The resulting solution is washed with 2 N sodium hydroxide solution and then with water, dried over sodium sulphate and evaporated in a waterpump vacuum. The residue is recrystallised from methanol/acetone, whereby 1-[2-(2-carbamoyl-phenoxy)-ethylamino]-3-(3-pyrazinyloxy)-2-propanol of melting point 130°–131° C. is obtained. The hydrochloride prepared therefrom with hydrochloric acid in ether is recrystallised from methanol/acetone; melting point 123°–124° C.

1-[N-[2-(2-carbamoyl-phenoxy)-ethyl]-N-benzylamino]-3-(2-chloro-3-pyrazinyloxy)-2-propanol, required as the starting material, is prepared as follows:

(a) Analogously to Example 23, 12.2 g of 2-N-benzylaminoethoxy)-benzamide and 11.2 g of 2-chloro-3-(2,3-epoxy-propoxy)-pyrazine give 1-[N-[2-(2-carbamoyl-phenoxy)-ethyl]-N-benzylamino]-3-(2-chloro-3-pyrazinyloxy)-2-propanol as an amorphous foam which is converted further as such.

EXAMPLE 30

Tablets containing 0.1 g of 1[-2-(2-carbamoyl-phenyloxy)-ethyl-amino]-3-(3-methyl-2-pyridyloxy)-2-propanol are prepared as follows:

| Composition (for 50,000 tablets): | |
|---|---|
| 1-[2-(2-carbamoyl-phenyloxy)-ethyl-amino]-3-(3-methyl-2-pyridyloxy)-2-propanol | 5000.00 g |
| lactose | 2980.00 g |
| maize starch | 3750.00 g |
| colloidal silica | 400.00 g |
| talc | 400.00 g |
| magnesium stearate | 50.00 g |
| water, q.s. | |

The 1-[2-(2-carbamoyl-phenyloxy)-ethyl-amino]-3-(3-methyl-2-pyridyloxy)-2-propanol is mixed with the lactose, with a part of the maize starch and with the colloidal silica and the mixture is forced through a sieve. A further part of the maize starch is worked to a paste with a five-fold amount of water on a waterbath and the powder mixture is kneaded with this paste until a slightly plastic mass is produced. This is forced through a sieve of about 3 mm mesh width and dried and the dry granules are again forced through a sieve. Thereafter, the remainder of the maize starch, the talc and the magnesium stearate are admixed and the resulting mixture is pressed to give tablets weighing 0.250 g (and having a breaking groove).

What is claimed is:

1. A cyclic-substituted derivative of 1-amino-2-propanol of the formula $$Ar_1-O-CH_2-\underset{OH}{\underset{|}{CH}}-CH_2-NH-Alk-O-Ar_2 \qquad (II)$$

wherein $Ar_1$ denotes phenyl substituted by lower alkyl or denotes pyrimidinyl and $Ar_2$ denotes phenyl substituted by carbamoyl or denotes pyrimidinyl with the proviso that $Ar_1$ denotes phenyl substituted by lower alkyl if $Ar_2$ denotes pyrimidinyl or $Ar_1$ denotes pyrimidinyl if $Ar_2$ denotes phenyl substituted by carbamoyl, and Alk represents lower alkylene which separates the nitrogen atom from the oxygen atom by at least two carbon atoms, such derivative being present in the form of a racemate, racemate mixture, optical antipodes or pharmaceutically usable salts thereof.

2. A compound of claim 1 which is 1-[2-(2-Pyrimidinyloxy)-ethylamino]-3-(2-methyl-phenyloxy)-2-propanol or pharmaceutically usable salts thereof.

3. The hydrogen oxalate salt of the compound of claim 2.

4. A compound of claim 1 which is 1-[2-(4-Carbamoylphenyloxy)-ethylamino]-3-(2-pyrimidinyloxy)-2-propanol or pharmaceutically usable salts thereof.

5. The hydrogen oxalate salt of the compound of claim 4.

6. A pharmaceutical preparation for producing a β-receptor-blocking, blood pressure lowering and vasodilatory effect in the treatment of arrythmias and angina pectoris in a warm-blooded animal, which comprises a therapeutically effective amount of a compound defined in claim 1, or a pharmaceutically usable salt thereof, together with a pharmaceutically usable excipient.

7. Method of producing a β-receptor-blocking, blood-pressure lowering and vasodilatory effect in the treatment of arrythmias and angina pectoris in a warm-blooded animal which comprises administering to said mammal an effective amount of one of the compounds of claim 1 or a pharmaceutically usable salt of such a compound.

* * * * *

UNITED STATES PATENT AND TRADEMARK OFFICE
CERTIFICATE OF CORRECTION

PATENT NO. : 4,139,623
DATED : February 13, 1979
INVENTOR(S) : KNUT A. JAEGGI et al It is certified that error appears in the above—identified patent and that said Letters Patent are hereby corrected as shown below:

Cover Page

Assignee: "C-G Corp." should be
--- CIBA-GEIGY Corporation---.

Signed and Sealed this

Twenty-fifth Day of September 1979

[SEAL]

Attest:

LUTRELLE F. PARKER
*Attesting Officer*    *Acting Commissioner of Patents and Trademarks*